United States Patent
Nakagami et al.

(10) Patent No.: US 11,529,474 B2
(45) Date of Patent: Dec. 20, 2022

(54) VALVED NEEDLE ASSEMBLY

(71) Applicant: NIPRO CORPORATION, Osaka (JP)

(72) Inventors: Hiroyuki Nakagami, Osaka (JP); Shingo Sakamoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 425 days.

(21) Appl. No.: 16/611,744

(22) PCT Filed: May 8, 2018

(86) PCT No.: PCT/JP2018/017720
§ 371 (c)(1),
(2) Date: Nov. 7, 2019

(87) PCT Pub. No.: WO2018/207758
PCT Pub. Date: Nov. 15, 2018

(65) Prior Publication Data
US 2021/0138162 A1    May 13, 2021

(30) Foreign Application Priority Data

May 8, 2017 (JP) .............................. JP2017-092497
Jan. 26, 2018 (JP) .............................. JP2018-012067

(51) Int. Cl.
*A61M 5/32* (2006.01)
*A61M 5/34* (2006.01)
*A61M 5/31* (2006.01)

(52) U.S. Cl.
CPC .......... *A61M 5/3293* (2013.01); *A61M 5/344* (2013.01); *A61M 2005/3128* (2013.01)

(58) Field of Classification Search
CPC .... A61M 5/3293; A61M 5/344; A61M 39/06; A61M 2005/31; A61M 2039/062; A61M 2039/064
See application file for complete search history.

(56) References Cited

U.S. PATENT DOCUMENTS

2004/0158208 A1*  8/2004  Hiejima ................ A61M 39/26
                                                                604/167.04

FOREIGN PATENT DOCUMENTS

EP    0 414 997 B1    3/1994
EP    1 452 201 A1    9/2004
(Continued)

OTHER PUBLICATIONS

Oct. 11, 2021 Office Action issued in Japanese Patent Application No. 2019-517625.
(Continued)

*Primary Examiner* — Nathan R Price
*Assistant Examiner* — Anh Bui
(74) *Attorney, Agent, or Firm* — Oliff PLC

(57) ABSTRACT

A valved needle assembly including a needle hub provided to a proximal end side of a hollow needle, and a valve member incorporated therein for blocking communication with the hollow needle. A protrusion protrudes from a distal end side toward a proximal end side inside the needle hub and the valve member blocks the proximal end side of the protrusion inside the needle hub. A central valve part of the valve member having a slit moves toward the protrusion such that the slit is opened and placed in communication by the protrusion. The central valve part includes a distal end tubular part and a proximal end tubular part extending from its outer circumferential portion toward the distal end side and the proximal end side respectively.

20 Claims, 9 Drawing Sheets

(56) References Cited

FOREIGN PATENT DOCUMENTS

| | | |
|---|---|---|
| JP | 2004-242763 A | 9/2004 |
| JP | 2012-130523 A | 7/2012 |
| JP | 2012130523 A * | 7/2012 |

OTHER PUBLICATIONS

Aug. 14, 2018 International Search Report issued in International Patent Application No. PCT/JP2018/017720.
Nov. 12, 2019 International Preliminary Reporton Patentability issued in International Patent Application No. PCT/JP2018/017720.

* cited by examiner

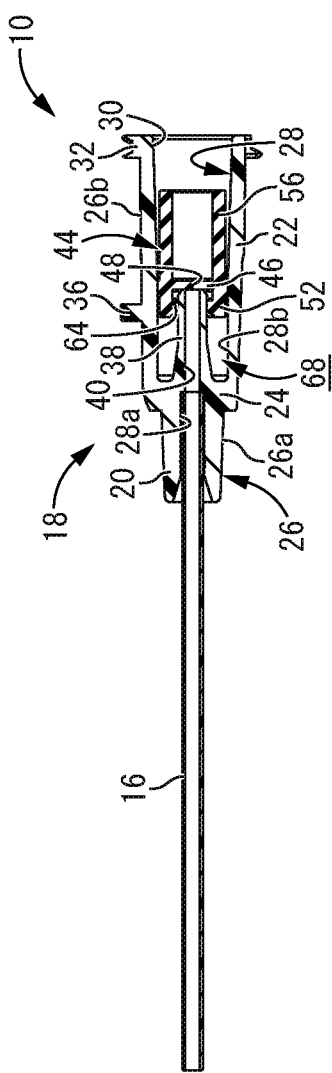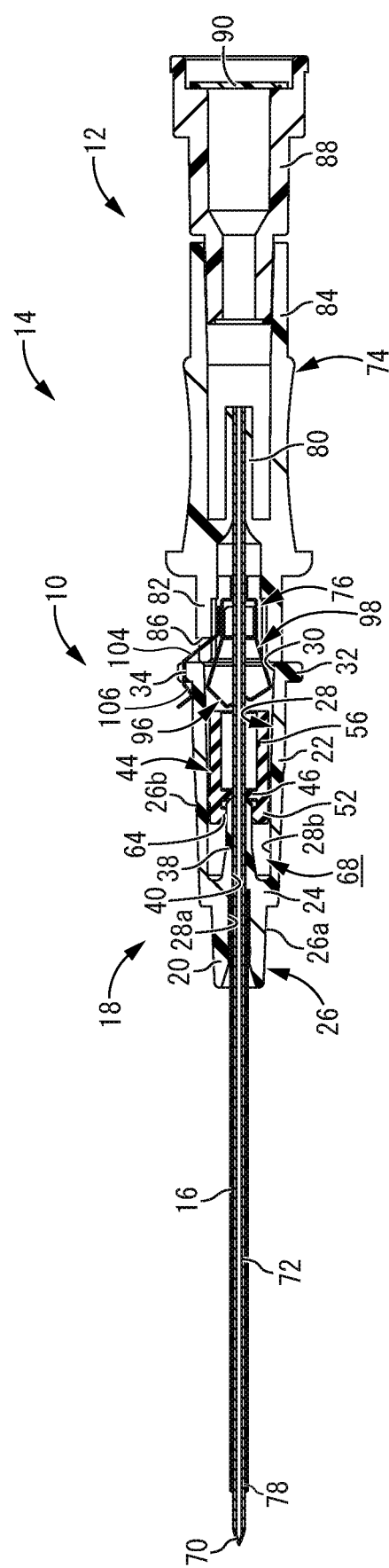

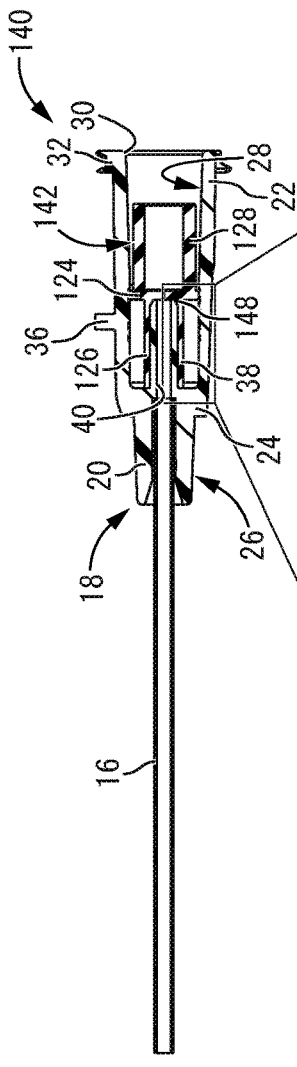

VALVED NEEDLE ASSEMBLY

TECHNICAL FIELD

The present invention relates generally to a needle assembly used when performing, for example, infusion, blood collection, hemodialysis and the like, and more particularly to a valved needle assembly provided with a valve for preventing leakage of blood or the like.

BACKGROUND ART

Conventionally, a valved needle assembly has been used for performing blood collection, blood transfusion, infusion, etc. on a patient. In such a valved needle assembly, a needle hub is provided on the proximal end side of the hollow needle so that a connector, a luer, or the like can be connected.

In addition, a valve member that blocks communication with the hollow needle is incorporated inside the needle hub, so as not to open the needle hole of the hollow needle to the atmosphere through the needle hub with no connector, luer, or the like connected. That is, the valve member is configured to prevent blood leakage when the needle assembly is stuck into the blood vessel of the patient, for example.

Meanwhile, such a valved needle assembly has a known structure as described in, for example, European Patent No. EP 0414997 (Patent Document 1).

BACKGROUND ART DOCUMENT

Patent Document

Patent Document 1: European Patent No. EP 0414997

SUMMARY OF THE INVENTION

Problem the Invention Attempts to Solve

It is an object of the present invention to provide a valved needle assembly with a novel structure, which is not encountered in the background art, so as to contribute to the enrichment of specific arts, and hence, products.

Means for Solving the Problem

A first preferred embodiment of the present invention provides a valved needle assembly including: a hollow needle; a needle hub provided to a proximal end side of the hollow needle; and a valve member incorporated inside the needle hub and blocking communication with the hollow needle, the valved needle assembly being characterized in that: a protrusion is provided inside the needle hub and protrudes from a distal end side toward a proximal end side, and the valve member blocks the proximal end side of the protrusion inside the needle hub; a central valve part of the valve member positioned in opposition to the protrusion and having a slit is configured to be moved toward the protrusion such that the slit is opened and placed in a communicating state by the protrusion; and the central valve part is provided with a distal end tubular part extending from an outer circumferential portion thereof toward the distal end side, and a proximal end tubular part extending from the outer circumferential portion thereof toward the proximal end side.

According to the valved needle assembly structured following the present preferred embodiment, the position of the valve member within the needle hub is stabilized by the tubular parts on the distal end side and the proximal end side respectively extending from the central valve part toward the inside and outside of the needle hub, thereby preventing excessive tilting of the valve member within the needle hub. This makes it possible to smoothly move the central valve part toward the protrusion, and the protrusion can be more accurately pressed against the central valve part, thereby stably opening the slit.

With this configuration, since a space is provided on the distal end side of the valve member inside the needle hub, the entire valve member including the central valve part can be easily moved toward the distal end side owing to the space on the distal end side.

A second preferred embodiment of the present invention provides the valved needle assembly according to the first preferred embodiment, wherein the valve member includes an outer circumferential guiding projection projecting on an outer circumferential surface of the valve member and configured to move in contact with an inner circumferential surface of the needle hub.

According to the valved needle assembly structured following to the present preferred embodiment, the guiding action during the movement of the valve member is improved, thereby further stabilizing the movement. That is, the central valve part of the valve member can be moved more straight in the axial direction with respect to the protrusion. Besides, sliding contact resistance may be reduced in comparison with the case where the entire outer circumferential surface of the valve member is brought into contact with the inner circumferential surface of the needle hub. Moreover, it is possible to avoid, for example, local floating of the valve member from the inner circumferential surface of the needle hub or the like, thereby stabilizing the contact state as well.

A third preferred embodiment of the present invention provides the valved needle assembly according to the first or second preferred embodiment, wherein an inner circumferential surface of the distal end tubular part of the valve member includes a guide surface that is in contact with an outer circumferential surface of the protrusion of the needle hub.

According to the valved needle assembly structured following the present preferred embodiment, the inner circumferential surface of the distal end tubular part of the valve member and the outer circumferential surface of the protrusion of the needle hub are in contact with each other to exhibit a guiding function. Thus, the central valve part of the valve member can be moved more straight toward the distal end side.

A fourth preferred embodiment of the present invention provides the valved needle assembly according to any of the first through third preferred embodiments, wherein the protrusion of the needle hub comprises a tubular protrusion formed in a tubular shape, and an inner circumferential surface of the distal end tubular part of the valve member includes a sealing face that is in contact with an outer circumferential surface of the tubular protrusion of the needle hub about an entire circumference.

According to the valved needle assembly configured structured following the present preferred embodiment, the inner circumferential surface of the distal end tubular part of the valve member and the outer circumferential surface of the tubular protrusion of the needle hub are in contact with each other about the entire circumference and exhibit sealing function. This may prevent blood from leaking into the needle hub (for example, the inside space on the distal end side of the valve member or the like) and pooling in the needle hub, or the like. In particular, by bringing the sealing face into contact with the tubular protrusion of the needle hub near the protruding end thereof, the space between the valve member and the tubular protrusion can be kept small, thereby effectively preventing pooling of the blood in that space.

A fifth preferred embodiment of the present invention provides the valved needle assembly according to the fourth preferred embodiment, wherein the distal end tubular part of the valve member includes an annular sealing projection projecting toward a radial inside, and an inner circumferential surface of the annular sealing projection comprises the sealing face.

According to the valved needle assembly structured following the present preferred embodiment, the annular sealing projection is provided on the distal end tubular part, and the inner circumferential surface of the annular sealing projection comprises the sealing face that is in contact with the outer circumferential surface of the tubular protrusion of the needle hub and exhibits the sealing function. Thus, in comparison with the case where the entire inner circumferential surface of the distal end tubular part is brought into contact with the outer circumferential surface of the tubular protrusion, a narrow sealing face is formed in the axial direction, and the sealing performance may be improved and stabilized.

A sixth preferred embodiment of the present invention provides the valved needle assembly according to the fourth or fifth preferred embodiment, wherein the distal end tubular part of the valve member includes a clamping fit part fitted externally onto the tubular protrusion in an expanded state in which the clamping fit part is pushed open, and an inner circumferential surface of the clamping fit part comprises the sealing face.

According to the valved needle assembly structured following the present preferred embodiment, the sealing can be even more reliably obtained by utilizing the clamping force due to the elasticity of the distal end tubular part. In addition, the present preferred embodiment can also be adopted in combination with the preceding fifth preferred embodiment, and the clamping fit part of the present preferred embodiment may be constituted by the annular sealing projection in the preceding fifth preferred embodiment.

A seventh preferred embodiment of the present invention provides the valved needle assembly according to any of the fourth through sixth preferred embodiments, wherein the distal end tubular part of the valve member includes a pressing projection projecting on an outer circumferential surface of the distal end tubular part and pressed against an inner circumferential surface of the needle hub, and the inner circumferential surface of the distal end tubular part is brought into contact with the outer circumferential surface of the tubular protrusion by a pressing reaction force of the pressing projection against the needle hub such that the sealing face is constituted.

According to the valved needle assembly structured following the present preferred embodiment, by utilizing the pressing reaction force of the pressing projection against the tubular protrusion of the needle hub, sealing between the inner circumferential surface of the distal end tubular part and the outer circumferential surface of the tubular protrusion can be reliably obtained. In addition, the present preferred embodiment can also be adopted in combination with the preceding fifth preferred embodiment or sixth preferred embodiment, whereby the sealing between the inner circumferential surface of the distal end tubular part and the outer circumferential surface of the tubular protrusion can also be obtained even more reliably.

An eighth preferred embodiment of the present invention provides the valved needle assembly according to any of the fourth through seventh preferred embodiments, wherein in the distal end tubular part of the valve member, a portion that does not constitute the sealing face is longer than a portion that constitutes the sealing face, and due to the central valve part of the valve member being moved toward the protrusion of the needle hub, the portion that does not constitute the sealing face is configured to deform in a corrugated shape in a lengthwise direction such that a length of the distal end tubular part is shortened.

According to the valved needle assembly structured following the present preferred embodiment, in the distal end tubular part, the length of the portion that does not constitute the sealing face with respect to the outer circumferential surface of the tubular protrusion is sufficiently obtained. Thus, when the central valve part of the valve member moves to the distal end side, it is possible to avoid increase in friction between the distal end tubular part and the tubular protrusion, thereby keeping insertion resistance small during inserting the connector or luer into the needle hub. In particular, when the valve member moves to the distal end side, the portion that does not constitute the sealing face in the distal end tubular part is deformed. Accordingly, the seal with respect to the outer circumferential surface of the tubular protrusion by means of the sealing face is maintained, thereby stably preventing blood leakage or the like.

A ninth preferred embodiment of the present invention provides the valved needle assembly according to any of the first through eighth preferred embodiments, wherein an outer circumferential surface of the valve member includes a compressing projection exerting a compression force on the slit of the valve member in a direction of closing by utilizing a contact reaction force against the needle hub due to contact with an inner circumferential surface of the needle hub.

According to the valved needle assembly structured following the present preferred embodiment, the closed state of the slit can be stably realized by utilizing the contact reaction force of the compressing projection against the inner circumferential surface of the needle hub. Thus, blood leakage during sticking of the needle assembly or the like can be effectively prevented.

A tenth preferred embodiment of the present invention provides the valved needle assembly according to any of the first through ninth preferred embodiments, wherein an air vent passage is provided and configured to discharge air in a space located in front of the valve member within the needle hub to an outside when the valve member moves to the distal end side within the needle hub.

According to the valved needle assembly structured following the present preferred embodiment, the air that exerts resistance to the movement of the valve member by remaining on the distal end side of the needle hub is actively discharged through the air vent passage. This may improve ease of operation during the movement of the valve member.

Besides, in the present preferred embodiment, it is preferable that the air vent passage is constituted by at least one of a gap provided between the inner circumferential surface of the needle hub and the outer circumferential surface of the valve member, and a through hole provided in the valve member. Also, the air vent passage communicating with the outside of the needle hub may be formed on the distal end side of the valve member.

With this configuration, the air vent passage can be easily formed, and the size of the air vent passage can also be adjusted.

In addition, in the valved needle assembly according to the present invention, it is preferable to provide a returning means for exerting an operating force in the direction in which the valve member is returned toward the original position before the movement in the state where the central valve part of the valve member is moved toward the protrusion and the slit is placed in communication.

With this configuration, it is possible to realize such a structure that, for example, after the valve member is moved and the slit is opened by an external force due to insertion of a male connector or the like, the male connector is removed, so that the valve member returns to the original position and the slit is automatically closed.

An eleventh preferred embodiment of the present invention provides the valved needle assembly according to any of the first through tenth preferred embodiments, wherein in the valve member, the distal end tubular part is thinner than the proximal end tubular part.

According to the valved needle assembly structured following the present preferred embodiment, for example, even in the case where the movement of the central valve part toward the protrusion is accompanied by deformation of the distal end tubular part, the deformation of the distal end tubular part may easily occur.

A twelfth preferred embodiment of the present invention provides the valved needle assembly according to any of the first through eleventh preferred embodiments, wherein the distal end tubular part of the valve member has a length that covers the protrusion of the needle hub as far as a distal end thereof.

According to the valved needle assembly structured following the present preferred embodiment, the protrusion of the needle hub is covered as far as its distal end by the distal end tubular part of the valve member, thereby more effectively preventing the valve member from tilting with respect to the needle hub.

A thirteenth preferred embodiment of the present invention provides the valved needle assembly according to any of the first through twelfth preferred embodiments, wherein the valve member includes a tapered part that gradually decreases in diameter from the central valve part toward the distal end tubular part, and on a radially inner side of the tapered part, a gap is provided between the tapered part and the protrusion of the needle hub.

According to the valved needle assembly structured following the present preferred embodiment, a gap is provided on the radially inner side of the tapered part, that is, between the central valve part and the distal end tubular part. Thus, even when a connector or a luer is inserted into the needle hub to induce deformation of the central valve part, it is possible to prevent a force exerted on the central valve part from being directly exerted on the distal end tubular part. Consequently, for example, even when a sealing face is provided on the distal end tubular part in combination with the preceding fourth preferred embodiment, the seal with respect to the outer circumferential surface of the tubular protrusion by the sealing face can be stably maintained regardless of the deformation of the central valve part.

A fourteenth preferred embodiment of the present invention provides the valved needle assembly according to any of the first through twelfth preferred embodiments, wherein an outer circumferential surface of a protruding end of the protrusion of the needle hub includes a tapered sloping face that gradually decreases in diameter toward the central valve part, and the valve member includes an overlapping part having a sloping inner face that gradually decreases in diameter from the distal end tubular part toward the central valve part while being in contact and overlapped with the tapered sloping face of the protrusion.

According to the valved needle assembly structured following the present preferred embodiment, the valve member includes the overlapping part and the overlapping part is overlapped with the outer circumferential surface of the protruding end of the protrusion of the needle hub. Thus, by the valve member being attached to the needle hub, the air between the valve member and the protrusion of the needle hub is pushed out, and when the infusion or blood transfusion is performed, it is possible to prevent the air between the valve member and the protrusion of the needle hub from entering the body of the patient.

A fifteenth preferred embodiment of the present invention provides the valved needle assembly according to any of the first through fourteenth preferred embodiments, wherein the valve member includes a connecting part that gradually increases in thickness dimension from the distal end tubular part toward the central valve part.

According to the valved needle assembly structured following the present preferred embodiment, the thickness dimension of the central valve part side in the connecting part can be sufficiently obtained while the thickness dimension of the distal end tubular part is kept small. With this configuration, for example, in the case where the distal end tubular part is deformed when the central valve part moves toward the protrusion, the deformation is effectively generated, while the deformation of the central valve part side portion of the connecting part is suppressed, thereby stably maintaining the shape of the said portion.

Further, in the valved needle assembly according to the present invention, it is preferable to provide a flanged part projecting to the radial outside at the distal end of the distal end tubular part of the valve member.

With this configuration, for example, in the case where the central valve part moves toward the protrusion so that the distal end tubular part is compressed in the axial direction and deformed by the inner circumferential surface of the needle hub, by the distal end tubular part being provided with a flanged part that projects to the radial outside at the distal end thereof, a sufficient contact area with the inner circumferential surface of the needle hub can be obtained. Thus, the compression and deformation of the distal end tubular part can be more reliably achieved.

A sixteenth preferred embodiment of the present invention provides a valved needle assembly including: a hollow needle; a needle hub provided to a proximal end side of the hollow needle; and a valve member incorporated inside the needle hub and blocking communication with the hollow needle, the valved needle assembly being characterized in that: a protrusion is provided inside the needle hub and protrudes from a distal end side toward a proximal end side, and the protrusion and the needle hub are integrally formed; the protrusion includes an axially middle section having a straight part with a generally constant outside diameter, and an axially distal end section extending from the axially middle section toward a distal end side of the needle hub while being thicker than the axially middle section; the valve member includes a central valve part positioned in opposition to the protrusion and having a slit, and a distal end tubular part extending from an outer circumferential portion of the central valve part toward the distal end side; and in a state where the valve member blocks the communication with the hollow needle, an inner circumferential surface of the distal end tubular part and an outer circumferential surface of the straight part are in close contact with each other such that an annular sealing face is provided.

According to the valved needle assembly structured following the present preferred embodiment, in a state where the valve member blocks the communication with the hollow needle, that is, in a state where no male connector or the like is connected to the needle hub, the inner circumferential surface of the distal end tubular part provided to the valve member and the outer circumferential surface of the straight part provided to the protrusion are in close contact with each other. With this configuration, the sealing between the valve member and the protrusion can be reliably obtained, thereby effectively preventing leakage and pooling of the blood to the distal end side of the valve member in the needle hub.

A seventeenth preferred embodiment of the present invention provides the valved needle assembly according to the sixteenth preferred embodiment, wherein in a state where the valve member moves to the distal end side and a proximal end portion of the needle hub and the hollow needle are held in communication with each other, the central valve part is in close contact with the outer circumferential surface of the straight part of the protrusion.

According to the valved needle assembly structured following the present preferred embodiment, for example, by a male connector or the like being connected, the valve member moves to the distal end side so that the proximal end portion of the needle hub and the hollow needle are held in communication with each other. Even in such a communicating state, since the central valve part of the valve member and the outer circumferential surface of the straight part provided to the protrusion are in close contact with each other, the sealing between the valve member and the protrusion is sufficiently obtained. This makes it possible to effectively prevent leakage or pooling of blood or liquid medicine toward the distal end side of the valve member within the needle hub.

An eighteenth preferred embodiment of the present invention provides a valved needle assembly including: a hollow needle; a needle hub provided to a proximal end side of the hollow needle; and a valve member incorporated inside the needle hub and blocking communication with the hollow needle, the valved needle assembly being characterized in that: a protrusion is provided inside the needle hub and protrudes from a distal end side toward a proximal end side, and the valve member blocks an inside of the needle hub; a central valve part of the valve member positioned in opposition to the protrusion and having a slit is configured to be moved toward the protrusion such that the slit is opened and placed in a communicating state by the protrusion; and the central valve part is provided with a proximal end tubular part extending from an outer circumferential portion thereof toward the proximal end side, and a compression force is exerted on an outer circumferential surface of the central valve part due to contact against the needle hub.

According to the valved needle assembly structured following the present preferred embodiment, due to the proximal end tubular part extending from the central valve part and contact of the outer circumferential surface of the central valve part against the needle hub, the position of the valve member within the needle hub can be stabilized. This makes it possible to move the central valve part smoothly toward the protrusion, and may stabilize the opening operation of the slit as well.

A nineteenth preferred embodiment of the present invention provides the valved needle assembly according to the eighteenth preferred embodiment, wherein an entirety of the valve member including the central valve part provided with the proximal end tubular part is positioned further on the proximal end side than a tip portion of the protrusion and housed inside the needle hub without fitting on an outer circumferential surface of the protrusion.

According to the valved needle assembly structured following the present preferred embodiment, a space sufficient to allow easy movement of the valve member to the distal end side can be obtained on the radially outer side of the protrusion inside the needle hub, thereby facilitating the opening operation of the valve member.

A twentieth preferred embodiment of the present invention provides a valved needle assembly including: a hollow needle; a needle hub provided to a proximal end side of the hollow needle; and a valve member incorporated inside the needle hub and blocking communication with the hollow needle, the valved needle assembly being characterized in that: a protrusion is provided inside the needle hub and protrudes from a distal end side toward a proximal end side, and the valve member blocks an inside of the needle hub; a central valve part of the valve member positioned in opposition to the protrusion and having a slit is configured to be moved toward the protrusion such that the slit is opened and placed in a communicating state by the protrusion; the central valve part is provided with a distal end tubular part extending from an outer circumferential portion thereof toward the distal end side, and a proximal end tubular part extending from the outer circumferential portion thereof toward the proximal end side; and the distal end tubular part extends as far as a distal end of the inside of the needle hub, and the distal end tubular part includes a sealing face that is in contact with a distal end outer circumferential surface of the protrusion about an entire circumference.

According to the valved needle assembly structured following the present preferred embodiment, owing to the distal end tubular part and the proximal end tubular part extending from the central valve part, tilting of the valve member or the like is suppressed, thereby stabilizing the position of the valve member within the needle hub. As a result, the central valve part can be smoothly moved toward the protrusion, and the opening operation of the slit may also be stabilized. Moreover, the sealing face is constituted by utilizing the fitted face between the distal end tubular part and the protrusion. Thus, the blood remaining in the needle hub is suppressed, and the sealing face may also stabilize the arrangement state of the valve member within the needle hub.

A twenty-first preferred embodiment of the present invention provides the valved needle assembly according to the twentieth preferred embodiment, wherein the distal end tubular part is in contact with only the distal end outer circumferential surface of the protrusion about the entire circumference in a compressed state, and due to the proximal end tubular part being pressed to the distal end side by an external instrument, a lengthwise middle portion of the distal end tubular part is configured to deform in a radial direction.

According to the valved needle assembly structured following the present preferred embodiment, due to the middle portion of the distal end tubular part that is located between the central valve part and the sealing face deforming to the radially outer side or the radially inner side, even if the distal end of the distal end tubular part hardly moves in the needle hub, the opening operation of the slit can be stably realized by the central valve part moving with respect to the protrusion. Therefore, it is also possible to realize a higher degree of liquid tightness due to a firm fitting state on the sealing face, for example, without impairing ease of opening operation of the slit.

Effect of the Invention

According to the present invention, it is possible to provide the valved needle assembly with a novel structure which is able to place the slit in an open state in association with the movement of the valve member.

BRIEF DESCRIPTION OF THE DRAWINGS

FIG. 1 is a vertical cross sectional view of a valved needle assembly according to a first practical embodiment of the present invention.

FIG. 2 is a vertical cross sectional view of an indwelling needle assembly including the valved needle assembly shown in FIG. 1, which is shown by a cross section different from that of FIG. 1.

FIG. 8A is a vertical cross sectional view showing another practical embodiment of the valved needle assembly shown in FIGS. 5A-5C, and FIG. 8B is an enlarged view of a principal part in FIG. 8A, and FIG. 8C is an enlarged view of an principal part of a valve member in the isolated state prior to attachment to a needle hub.

EMBODIMENTS FOR CARRYING OUT THE INVENTION

In order to clarify the present invention more specifically, practical embodiments of the present invention will be described in detail below in reference to the drawings.

Figure 3:
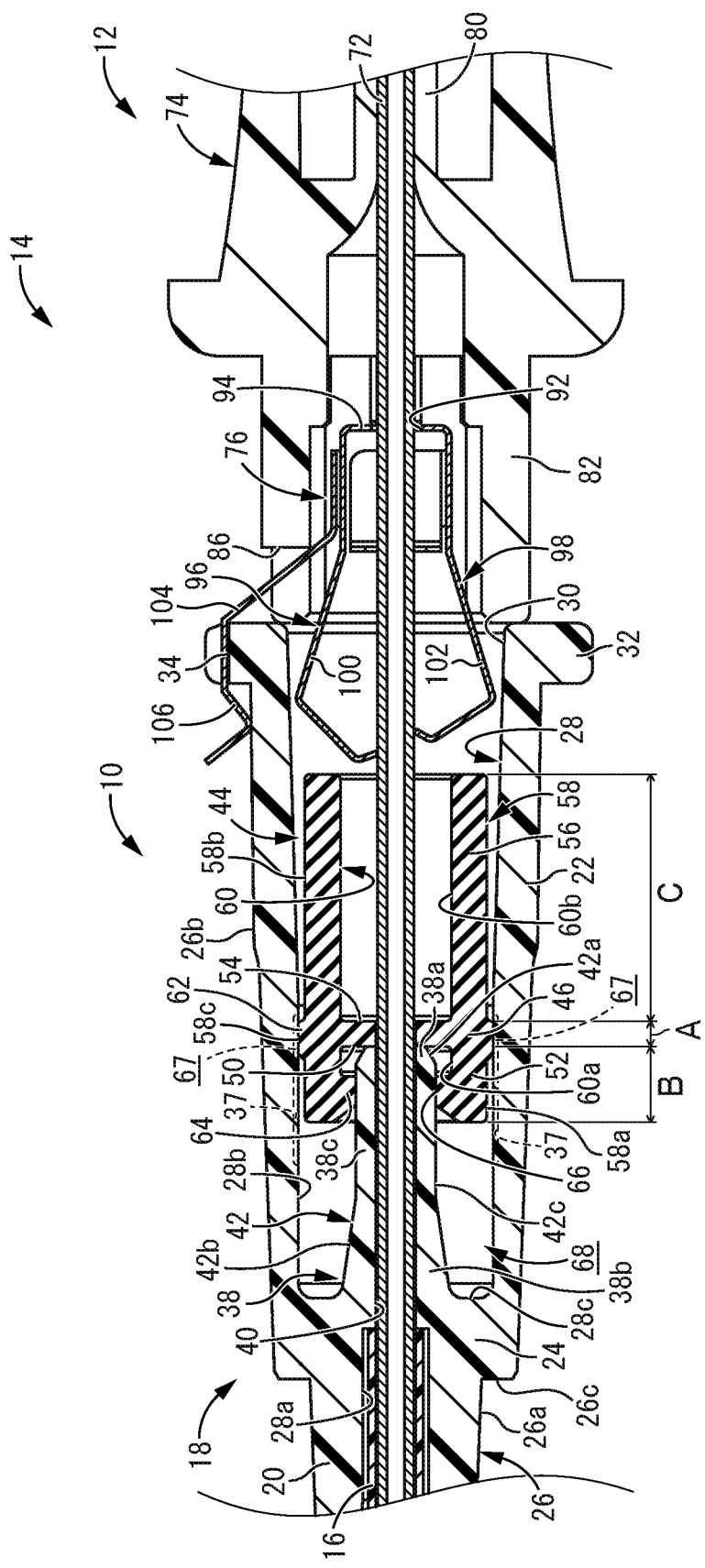
FIG. 3 is an enlarged vertical cross sectional view of a principal part in FIG. 2.

First, FIG. 1 depicts an outer needle 10 as a first practical embodiment of a valved needle assembly according to the present invention. As depicted in FIGS. 2 and 3, the outer needle 10 is constituted as an indwelling needle assembly 14 by an inner needle 12 being inserted therein. After the indwelling needle assembly 14 is stuck into the skin of the patient, the inner needle 12 is pull out of the outer needle 10, so that the outer needle 10 is inserted percutaneously and indwelled in the blood vessel of the patient. In the following description, the axial direction refers to the left-right direction in FIG. 1 that is the central axis direction of the outer needle 10. Besides, the distal end side refers to the left side in FIG. 1 that is the side stuck into the patient, while the proximal end side refers to the right side in FIG. 1 that is the side grasped by the user.

Described more specifically, the outer needle 10 includes an outer needle main body 16 serving as a hollow needle and an outer needle hub 18 serving as a needle hub. The outer needle main body 16 of the present practical embodiment is a hollow needle formed of a soft synthetic resin and has flexibility. The proximal end portion of the outer needle main body 16 is inserted from the distal end side of the outer needle hub 18, and the outer needle main body 16 is fixedly supported by the outer needle hub 18. The inside diameter dimension of the outer needle main body 16 is slightly larger than the outside diameter dimension of an inner needle main body 72 of the inner needle 12 described later.

The outer needle hub 18 has a roughly tubular shape overall, and is formed of a rigid synthetic resin. In the present practical embodiment, the outer needle hub 18 has a roughly stepped tubular shape, and its distal end side constitutes a small-diameter tube part 20, while the proximal end side constitutes a large-diameter tube part 22. The small-diameter tube part 20 is smaller in both inside diameter dimension and outside diameter dimension than the large-diameter tube part 22, and the small-diameter tube part 20 and the large-diameter tube part 22 are connected by an intermediate wall 24 having an annular shape that expands in the radial direction.

That is, the proximal end portion of the outer needle main body 16 is inserted into the small-diameter tube part 20 of the outer needle hub 18, and is fixed by being subjected to a process such as bonding as necessary.

In addition, an outer circumferential surface 26 of the outer needle hub 18 includes an outer circumferential surface 26a of the small-diameter tube part 20, an outer circumferential surface 26b of the large-diameter tube part 22, and a distal side end face 26c of the intermediate wall 24. Meanwhile, an inner circumferential surface 28 of the outer needle hub 18 includes an inner circumferential surface 28a of the small-diameter tube part 20, an inner circumferential surface 28b of the large-diameter tube part 22, and a proximal side end face 28c of the intermediate wall 24. In the present practical embodiment, the outer circumferential surface 26b and the inner circumferential surface 28b of the large-diameter tube part 22 each have a tapered surface shape overall in which the outside diameter dimension and the inside diameter dimension thereof gradually increase toward the proximal end side. In particular, the inner circumferential surface 28b of the large-diameter tube part 22 is configured such that the distal end side from the axially center portion has a generally constant inside diameter dimension, while the proximal end side from the axially center portion has an inside diameter dimension gradually increasing toward the proximal end side.

Moreover, the outer circumferential surface 26 (26b) of a proximal end opening part 30 of the outer needle hub 18 is provided with a flange 32 that projects to the radially outer side. The flange 32 has a generally annular shape extending over roughly the entire circumference in the circumferential direction, and includes a male screw on its outer circumferential surface. Accordingly, a luer-lock type male connector can be connected to the proximal end opening part 30 of the outer needle hub 18. Besides, an engaging groove 34 extending in the axial direction is formed on a part of the circumference of the flange 32 (upper side in FIGS. 2 and 3).

Furthermore, a projecting operation piece 36 that projects to the radially outer side is provided on the outer circumferential surface 26b in the axially middle portion of the large-diameter tube part 22. The projecting operation piece 36 has a predetermined circumferential dimension, and in the present practical embodiment, is formed on a part of the circumference (upper side in FIG. 1).

Additionally, a concave groove 37 that opens to the radially inner side and extends in the axial direction is formed on the inner circumferential surface 28b in the axially middle portion of the large-diameter tube part 22. The concave groove 37 has a circumferential dimension that is less than once around the circumference in the circumferential direction. One or a plurality of the concave grooves 37 are formed on the inner circumferential surface 28b of the large-diameter tube part 22 so as to have an appropriate remote distance. The axial dimension of the concave groove 37 can be set according to, for example, the movement distance in the axial direction of a valve member 44 described later.

Here, in the present practical embodiment, inside the outer needle hub 18 and on the proximal side end face 28c of the intermediate wall 24, a tubular protrusion 38 serving as a protrusion of round tubular shape is integrally formed with the outer needle hub 18 so as to protrude from the distal end side toward the proximal end side. The tubular protrusion 38 is provided in the center of the intermediate wall 24, and is penetrated by a center hole 40 in the axial direction. That is, the center hole 40 passes through the intermediate wall 24 and the tubular protrusion 38, and the distal end side of the center hole 40 opens onto the distal side end face 26c of the intermediate wall 24, so that the center hole 40 and the inner hole of the small-diameter tube part 20 communicate with each other. On the other hand, the proximal end side of the center hole 40 opens onto the protruding end face (proximal side end face) of the tubular protrusion 38, and the center hole 40 and the inner hole of the large-diameter tube part 22 communicate with each other. Namely, the inner hole of the small-diameter tube part 20 and the inner hole of the large-diameter tube part 22 communicate with each other via the center hole 40 of the tubular protrusion 38.

The inside diameter dimension of the tubular protrusion 38 (center hole 40) is generally constant in the axial direction, while being slightly larger than the inner needle main body 72 of the inner needle 12 described later, and being roughly equal to the inside diameter dimension of the outer needle main body 16. On the other hand, in the present practical embodiment, the outer circumferential surface 42 of the tubular protrusion 38 is configured such that the outside diameter dimension of an outer circumferential surface 42a of the axially proximal end section (protruding tip end) 38a has a tapered surface shape whose outside diameter dimension gradually decreases toward the proximal end side so as to easily push open a slit 48 described later. That is, the outer circumferential surface 42a of the protruding tip end 38a of the tubular protrusion 38 is constituted by a tapered sloping face that gradually decreases in diameter toward the protruding tip side (the side of a central valve part 46 of a valve member 44 described later). At the same time, an outer circumferential surface 42b of the axially distal end section (protruding base end) 38b has a tapered surface shape whose outside diameter dimension gradually increases toward the distal end side. Besides, an axially middle section of the tubular protrusion 38 includes a straight part 38c in which the outside diameter dimension of an outer circumferential surface 42c is generally constant across roughly the entire length thereof. In particular, in the present practical embodiment, since the inside diameter dimension of the center hole 40 is generally constant in the axial direction, the circumferential wall of the tubular protrusion 38 is thicker in an axially distal end section 38b rather than in the axially middle section (straight part) 38c.

Inside the outer needle hub 18 having the structure as described above, a valve member 44 is incorporated. The valve member 44 has a generally sleeve shape (roughly tubular shape) overall, and is formed of a rubber such as silicone rubber or isoprene rubber, or an elastic body such as an elastomer.

The valve member 44 includes a central valve part 46 of generally circular disk shape at an axially middle portion. The central valve part 46 has a disk shape with a generally constant thickness dimension, and is penetrated in the thickness direction by a slit 48 formed at the central portion thereof. The slit 48 of the present practical embodiment has a straight-line shape extending in the front-rear direction of the paper surface in FIG. 1, but may alternatively be a cross shape, a radial shape extending from the center in a plurality of directions (for example, three directions), or the like. The diametrical dimension of the slit 48 (the dimension in the front-rear direction of the paper surface in FIG. 1) is smaller than the inside diameter dimensions of a distal end tubular part 52 and a proximal end tubular part 56 described later.

The central valve part 46 is provided with a distal end tubular part 52 of generally tubular shape extending from the outer circumferential portion of its distal side end face 50 toward the distal end side, namely the outer needle main body 16 side, and a proximal end tubular part 56 of generally tubular shape extending from the outer circumferential portion of its proximal side end face 54 toward the proximal end side, namely the proximal end opening part 30 side. That is, the valve member 44 of generally sleeve shape is constituted by including the distal end tubular part 52, the proximal end tubular part 56, and the central valve part 46. Therefore, an outer circumferential surface 58 of the valve member 44 includes an outer circumferential surface 58a of the distal end tubular part 52, an outer circumferential surface 58b of the proximal end tubular part 56, and an outer circumferential surface 58c of the central valve part 46. On the other hand, an inner circumferential surface 60 of the valve member 44 includes an inner circumferential surface 60a of the distal end tubular part 52 and an inner circumferential surface 60b of the proximal end tubular part 56.

In the present practical embodiment, the inside diameter dimension and the outside diameter dimension of the distal end tubular part 52 are generally constant in the axial direction, so that the distal end tubular part 52 has a tubular shape extending roughly straight in the axial direction. In addition, the inside diameter dimension and the outside diameter dimension of the proximal end tubular part 56 are also generally constant in the axial direction, so that the proximal end tubular part 56 also has a tubular shape extending roughly straight in the axial direction. In particular, in the present practical embodiment, the inside diameter dimension of the distal end tubular part 52 and the inside diameter dimension of the proximal end tubular part 56 are roughly equal, and the outside diameter dimension of the distal end tubular part 52 and the outside diameter dimension of the proximal end tubular part 56 are roughly equal. Such outside diameter dimensions of the distal end tubular part 52 and the proximal end tubular part 56 are slightly smaller than the inside diameter dimension of the large-diameter tube part 22 of the outer needle hub 18. On the other hand, the inside diameter dimensions of the distal end tubular part 52 and the proximal end tubular part 56 are roughly equal to the maximum outside diameter dimension of the tubular protrusion 38 of the outer needle hub 18. That is, the inside diameter dimensions of the distal end tubular part 52 and the proximal end tubular part 56 are larger than the outside diameter dimension of the tubular protrusion 38 over roughly the entire tubular protrusion 38.

Moreover, the central valve part 46 includes at its outer circumferential end an outer circumferential guiding projection 62 that projects to the radially outer side. The outer circumferential guiding projection 62 has a generally annular shape continuously extending about the entire circumference in the circumferential direction, and the outside diameter dimension thereof is larger than the outside diameter dimensions of the distal end tubular part 52 and the proximal end tubular part 56. With this configuration, the outer circumferential surface 58*c* of the central valve part 46 is constituted by the outer circumferential surface of the outer circumferential guiding projection 62. In other words, the outer circumferential guiding projection 62 is formed on the outer circumferential surface 58 of the valve member 44 so as to project to the radially outer side. In the present practical embodiment, in the isolated state of the valve member 44 prior to attachment to the outer needle hub 18, the outside diameter dimension of the outer circumferential guiding projection 62 is larger than the inside diameter dimension of the portion of the inner circumferential surface 28*b* of the large-diameter tube part 22 of the outer needle hub 18 where the inside diameter dimension is generally constant.

Furthermore, although the axial dimensions of the distal end tubular part 52 and the proximal end tubular part 56 are not limited in any way, it is preferable that the axial dimension B of the distal end tubular part 52 (see FIG. 3) is larger than the axial dimension A of the central valve part 46 (see FIG. 3). Besides, it is desirable that the maximum dimension of the axial dimension B be configured such that the distal end of the distal end tubular part 52 does not hit the inner surface (proximal side end face 28*c*) of the intermediate wall 24 of the outer needle hub 18 even when the valve member 44 moves forward. Moreover, it is preferable that the axial dimension C of the proximal end tubular part 56 (see FIG. 3) is larger than the axial dimension A of the central valve part 46. Further, in the attached state of the valve member 44 to the outer needle hub 18 described later, the axial dimension from the proximal end opening part 30 to the proximal side end face of the proximal end tubular part 56 can be set according to the insertion length of a male connector 108 or the like to be inserted into the outer needle hub 18. For example, in the case of adopting a male connector in accordance with the ISO standards, the axial dimension from the proximal end opening part 30 to the proximal side end face of the proximal end tubular part 56 can be set to, for example, about 4 to 6 mm so that when the male connector 108 is inserted from the proximal end opening part 30 for a length of 7.5 mm, the central valve part 46 moves to the tubular protrusion 38 side and opens the slit 48.

Here, the inner circumferential surface 60*a* of the distal end portion of the distal end tubular part 52 includes an annular sealing projection 64 projecting toward the radial inside. The annular sealing projection 64 is formed continuously about the entire circumference in the circumferential direction, and its distal side end face comprises a tapered surface sloping radially inward toward the proximal end side while its proximal side end face comprises a flat surface generally perpendicular to the axial direction. That is, the inside diameter dimension of the distal end tubular part 52 is reduced at the site where the annular sealing projection 64 is formed. Therefore, the inner circumferential surface 60*a* of the distal end tubular part 52 includes an inner circumferential surface 66 of the annular sealing projection 64 having a smaller inside diameter dimension. In the present practical embodiment, in the isolated state of the valve member 44 prior to attachment to the outer needle hub 18, the inside diameter dimension of the annular sealing projection 64 is roughly equal to or slightly smaller than the outside diameter dimension of the straight part 38*c* of the tubular protrusion 38.

The valve member 44 having such a structure is incorporated inside the outer needle hub 18 with the outer needle main body 16 supported at the tip, namely, inside the large-diameter tube part 22, so that the outer needle 10 of the present practical embodiment is provided. Then, the protruding tip end of the tubular protrusion 38 of the outer needle hub 18 is inserted from the distal end side of the valve member 44, and the protruding tip end face of the tubular protrusion 38 and the distal side end face 50 of the central valve part 46 of the valve member 44 are in contact with each other. That is, the tubular protrusion 38 and the central valve part 46 are in opposition to each other in the axial direction, and the slit 48 is formed in the central valve part 46 at the position opposed to the tubular protrusion 38 in the axial direction.

Here, the outside diameter dimension of the outer circumferential guiding projection 62 of the valve member 44 in the isolated state is larger than the inside diameter dimension of the portion of the inner circumferential surface 28*b* of the large-diameter tube part 22 where the inside diameter dimension is generally constant. Thus, due to the valve member 44 being incorporated in the large-diameter tube part 22, the outer circumferential guiding projection 62 is compressed radially inward. In the present practical embodiment, the outside diameter dimension of the valve member 44 other than the formation position of the outer circumferential guiding projection 62 is slightly smaller than the inside diameter dimension of the large-diameter tube part 22. Accordingly, radially between the valve member 44 and the large-diameter tube part 22, there are formed annular gaps on the axially opposite sides of the outer circumferential guiding projection 62 (namely, on the radially outer sides of the distal end tubular part 52 and the proximal end tubular part 56).

Further, in the present practical embodiment, the concave groove 37 of the inner circumferential surface 28 (28*b*) of the outer needle hub 18 and the outer circumferential guiding projection 62 of the valve member 44 are provided at positions overlapping with each other in the axial direction. That is, the outer circumferential guiding projection 62 of the valve member 44 is configured to be compressed radially inward by a portion that is away from the concave groove 37 of the inner circumferential surface 28*b* of the large-diameter tube part 22 in the circumferential direction. On the other hand, at the formation position of the concave groove 37, the outer circumferential surface 58*c* of the outer circumferential guiding projection 62 and the inner circumferential surface 28*b* of the large-diameter tube part 22 (groove bottom face of the concave groove 37) are not in contact with each other. Accordingly, due to the opening of the concave groove 37 being covered by the outer circumferential guiding projection 62 between the two opposed surfaces 58c and 28b, a tunnel-shaped gap 67 is formed. Therefore, the gap formed radially between the distal end tubular part 52 and the large-diameter tube part 22 on the distal end side of the outer circumferential guiding projection 62 and the gap formed radially between the proximal end tubular part 56 and the large-diameter tube part 22 on the proximal end side of the outer circumferential guiding projection 62 communicate with each other through the concave groove 37 (gap 67). That is, the concave groove 37 (gap 67) forms an air vent passage for discharging air in a space 68 (described later) on the distal end side of the valve member 44 to the outside when the valve member 44 moves to the distal end side.

In this way, at the formation position of the outer circumferential guiding projection 62, due to the valve member 44 being compressed radially inward by the large-diameter tube part 22, the slit 48 provided in the central valve part 46 positioned on the radially inner side of the outer circumferential guiding projection 62 is stably in the closed state. Specifically, in the present practical embodiment, the outer circumferential guiding projection 62 constitutes a compressing projection for coming into contact with the inner circumferential surface 28b of the large-diameter tube part 22 of the outer needle hub 18 and exerting a compression force on the slit 48 in the direction of closing by utilizing the contact reaction force.

In the initial state of the outer needle 10 shown in FIG. 1 (namely, before insertion of the male connector 108 described later), the slit 48 is in the closed state on the proximal end side of the tubular protrusion 38 inside the outer needle hub 18, thereby blocking communication from the inside of the large-diameter tube part 22 to the inner hole of the outer needle main body 16.

Also, in this initial state, the annular sealing projection 64 provided at the distal end of the valve member 44 is located on the radially outer side of the tubular protrusion 38 in the outer needle hub 18. In the present practical embodiment, the annular sealing projection 64 is located on the protruding tip end side (axially proximal end side) of the straight part 38c formed in the axially middle section of the tubular protrusion 38.

Here, the inside diameter dimension of the annular sealing projection 64 of the valve member 44 in the isolated state is smaller than the outside diameter dimension of the straight part 38c of the tubular protrusion 38. Thus, in the attached state of the valve member 44 and the outer needle hub 18, the annular sealing projection 64 is in contact with the outer circumferential surface 42c of the straight part 38c of the tubular protrusion 38 about the entire circumference, and is compressed by the tubular protrusion 38 so as to be pushed open to the radially outer side. In other words, the annular sealing projection 64 is fitted externally onto the tubular protrusion 38 in an expanded state in which the annular sealing projection 64 is pushed open to the radially outer side. The tubular protrusion 38 is clamped by the annular sealing projection 64 from the radially outer side, so that the inner circumferential surface 66 of the annular sealing projection 64 and the outer circumferential surface 42c of the straight part 38c of the tubular protrusion 38 are in close contact with each other. Therefore, in the present practical embodiment, the annular sealing projection 64 constitutes a clamping fit part fitted externally onto the tubular protrusion 38 in the expanded state in which the clamping fit part is pushed open. This configuration provides a liquid-tight sealing between the inner circumferential surface 66 of the annular sealing projection 64 and the outer circumferential surface 42c of the straight part 38c of the tubular protrusion 38 about the entire circumference. Accordingly, the inner circumferential surface 66 of the annular sealing projection 64 and the outer circumferential surface 42c of the straight part 38c of the tubular protrusion 38 each comprise annular sealing faces.

In this way, due to the annular sealing projection 64 positioned at the distal end of the valve member 44 being located near the protruding tip end of the tubular protrusion 38, on the distal end side of the valve member 44, there is formed a generally annular space 68 on the radially outer side of the protruding base end portion of the tubular protrusion 38 with a predetermined axial dimension.

The outer needle 10 of the present practical embodiment having such a structure is used as the indwelling needle assembly 14 in combination with the inner needle 12 as shown in FIGS. 2 and 3.

The inner needle 12 includes an inner needle main body 72 having a sharp needle tip 70 at its distal end, an inner needle hub 74 attached to the proximal end of the inner needle main body 72, and a needle tip protector 76 mounted so as to be movable in the axial direction with respect to the inner needle main body 72.

In the present practical embodiment, the inner needle main body 72 is a hollow needle, and is formed of a known material such as stainless steel, aluminum, titanium, or an alloy thereof. The needle tip 70 provided at the distal end of the inner needle main body 72 includes an inclined surface that is inclined with respect to the axial direction, thereby making it possible to puncture a living body with ease and low stimulation. Besides, on the outer circumferential surface of the distal end portion of the inner needle main body 72, there is formed a large-diameter part 78 whose outside diameter dimension is made large. The large-diameter part 78 may be formed about the entire circumference in the circumferential direction by manufacturing the inner needle main body 72 by centerless process or the like, or alternatively, a pair of large-diameter parts 78, 78 may be formed by performing crushing processing on the inner needle main body 72. Further, the inner needle main body 72 may be a solid needle.

On the other hand, the inner needle hub 74 attached to the proximal end of the inner needle main body 72 has a generally tubular shape overall, and is integrally formed of a rigid synthetic resin. The axially middle portion of the inner needle hub 74 has a double cylinder structure in which an outer cylinder is placed externally about an inner cylinder. The proximal end of the inner needle main body 72 is inserted into a fixing tube part 80, which is the inner cylinder, and a treatment such as bonding is performed as necessary, whereby the inner needle main body 72 is fixedly supported with respect to the inner needle hub 74. Further, from the outer cylinder of the double cylinder structure, a housing tube part 82 extends to the distal end side, and a coupling tube part 84 extends to the proximal end side. In addition, on the distal end of the housing tube part 82, there is formed a notch 86 opening to the distal end side in a part of the circumference (upper side in FIGS. 2 and 3).

Moreover, an inner needle cap 88 is detachably attached to the proximal end opening part of the coupling tube part 84. The inner needle cap 88 is a synthetic resin member having a generally stepped round tubular shape in which a stepped part is provided in the axially middle portion. Inside the inner needle cap 88, there is provided a ventilation filter 90, and the ventilation filter 90 has a property of transmitting gas but blocking liquid. Due to the inner needle cap 88 being attached to the coupling tube part 84, the proximal end opening part of the inner needle hub 74 is covered liquid-tightly, so that blood return through the inner needle main body 72 does not leak out to the outside. In addition, by the inner needle hub 74 and the inner needle cap 88 being made of transparent members, confirmation of blood return (flashback) can be easily performed.

The needle tip protector 76 provided in the inner needle 12 includes a proximal end wall 94 having an insertion hole 92 at the center on the proximal end, and the inside diameter dimension of the insertion hole 92 is smaller than the outside diameter dimension of the large-diameter part 78 of the inner needle main body 72, and is larger than the outside diameter dimension of the portion other than the large-diameter part 78 of the inner needle main body 72. Besides, a pair of arm pieces 96, 98 extend from the end edges on both sides of the insertion hole 92 of the proximal end wall 94 (both sides in the vertical direction in FIGS. 2 and 3) to the distal end side. The distal end sides of the pair of arm pieces 96, 98 comprise elastic pieces 100, 102 that easily undergo elastic deformation in the radial direction. Additionally, in one arm piece 96 (upper arm piece in FIGS. 2 and 3), from the portion which is less likely to undergo elastic deformation on the proximal end side, an engaging piece 104 extends so as to project radially outward and bend at its projecting tip end (radially outer side end), then extends to the distal end side. Furthermore, at the distal end of the engaging piece 104, there is formed an engaging claw part 106 bending radially inward.

The proximal end of the inner needle main body 72 having the above structure is fixed to the inner needle hub 74, and the needle tip protector 76 is externally mounted about the inner needle main body 72, whereby the inner needle 12 of the present practical embodiment is constituted. The indwelling needle assembly 14 of the present practical embodiment is constituted by inserting the inner needle 12 through the outer needle 10.

That is, the needle tip protector 76 through which the inner needle main body 72 is inserted is housed in the housing tube part 82 of the inner needle hub 74, while the inner needle main body 72 extending to the distal end side is inserted from the proximal end opening part 30 of the outer needle 10, and penetrates the valve member 44 through the slit 48 provided in the central valve part 46 of the valve member 44, so as to be inserted from the proximal end side toward the distal end side with respect to the outer needle 10.

In the attached state of the outer needle 10 and the inner needle 12, the elastic pieces 100, 102 are elastically deformed to the radially outer side by the inner needle main body 72. That is, an urging force based on a recovering deformation to the radially inner side is exerted on the elastic pieces 100, 102, and the deformation of the elastic pieces 100, 102 to the radially inner side based on the urging force is restricted by contact with the inner needle main body 72.

Besides, the engaging piece 104 extending from the arm piece 96 extends to the radially outer side through the notch 86 provided in the housing tube part 82, and is inserted into the engaging groove 34 provided in the flange 32 of the proximal end opening part 30 of the outer needle hub 18. Accordingly, the engaging claw part 106 provided to the distal end of the engaging piece 104 and the flange 32 are engaged. With this configuration, in the attached state of the outer needle 10 and the inner needle 12, the needle tip protector 76 and the outer needle hub 18 are connected to each other.

The indwelling needle assembly 14 having the above structure is stuck into the skin of the patient with the outer needle 10 and the inner needle 12 combined as shown in FIGS. 2 and 3. Then, by the inner needle 12 being pulled out, the outer needle 10 is percutaneously indwelled in the blood vessel of the patient in the state shown in FIG. 1.

Here, due to the inner needle 12 being pulled out, the contact between the inner needle main body 72 and the elastic pieces 100, 102 is released, and the elastic pieces 100, 102 are moved to the radially inner side according to the urging force. By so doing, the elastic pieces 100, 102 are moved on the needle axis of the inner needle main body 72, and the needle tip 70 of the inner needle main body 72 is covered and protected by the elastic pieces 100, 102. Further, the movement of the inner needle main body 72 toward the distal end side with respect to the needle tip protector 76 after the inner needle 12 is pulled out can be limited.

Moreover, due to the elastic pieces 100, 102 moving to the radially inner side, a gap is formed between the elastic piece 100 and the outer needle hub 18 so that the engagement between the flange 32 and the engaging claw part 106 can be released. That is, in the needle tip protector 76 of the present practical embodiment, due to the withdrawal of the inner needle 12 from the outer needle 10, the needle tip 70 of the inner needle main body 72 is protected by the needle tip protector 76, and the connection between the needle tip protector 76 and the outer needle hub 18 can also be released.

Furthermore, by pulling out the inner needle main body 72, the proximal end wall 94 of the needle tip protector 76 and the large-diameter part 78 of the inner needle main body 72 are engaged. Accordingly, the movement of the inner needle main body 72 toward the proximal end side with respect to the needle tip protector 76 is also limited. Therefore, in the indwelling needle assembly 14 of the present practical embodiment, the inner needle 12 can be detached from the outer needle 10 with the needle tip 70 of the inner needle main body 72 protected by the needle tip protector 76.

Figure 4:
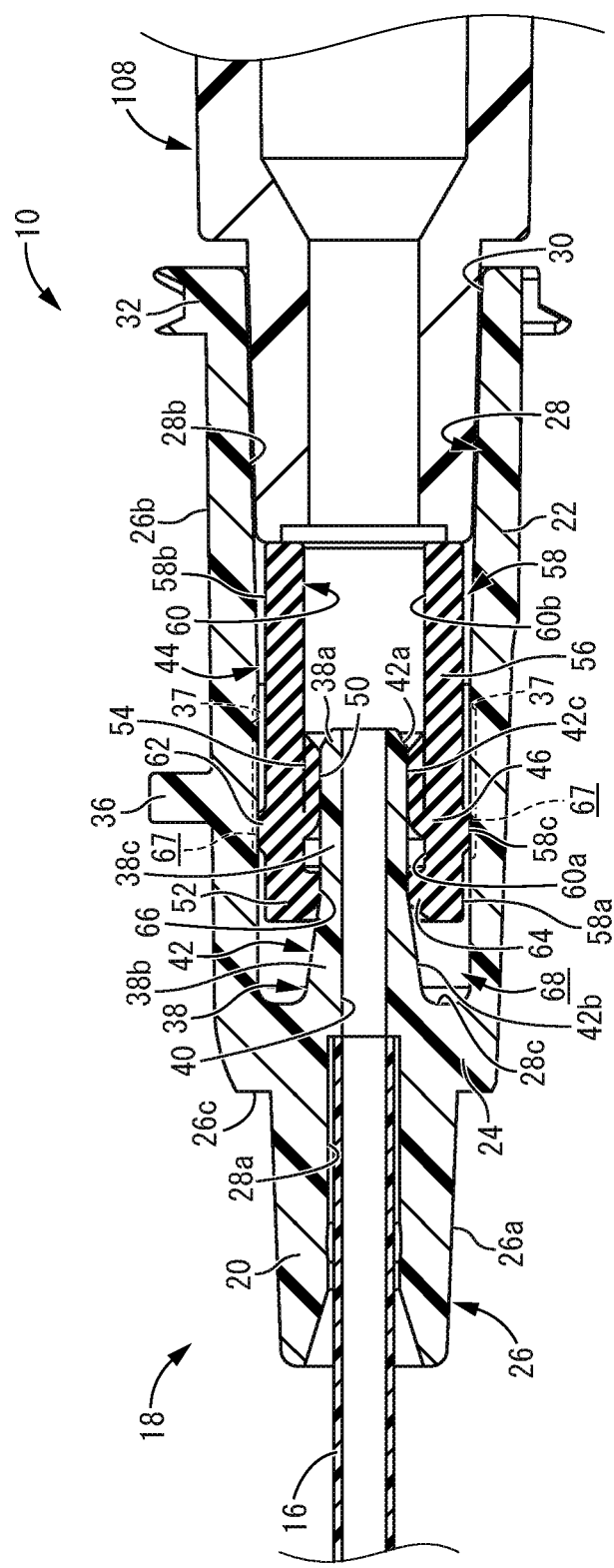
FIG. 4 is an enlarged vertical cross sectional view of the valved needle assembly shown in FIG. 1 with a male connector inserted.

Then, as shown in FIG. 4, by connecting the male connector 108 such as a syringe from the proximal end opening part 30 of the outer needle hub 18 of the outer needle 10 indwelled in the blood vessel of the patient, the distal end of the male connector 108 is brought into direct contact with the proximal end tubular part 56 of the valve member 44. By so doing, the valve member 44 is pushed into the distal end side, and the entire valve member 44 is moved toward the space 68 on the distal end side. That is, the central valve part 46 of the valve member 44 is moved to the distal end side toward the tubular protrusion 38 of the outer needle hub 18, so that the slit 48 is pushed open by the tubular protrusion 38. In specific terms, the wall parts on both sides of the slit 48 in the central valve part 46 are deformed so as to bend to the proximal end side, and the distal side end face 50 of the central valve part 46 comes into close contact with the outer circumferential surface 42c of the straight part 38c of the tubular protrusion 38. Accordingly, the slit 48 is placed in the opened state, and the inside of the outer needle main body 16 and the inside of the male connector 108 communicate with each other through the inside of the proximal end portion of the outer needle hub 18, namely, the inside of the valve member 44. Then, infusion, blood transfusion, blood collection, and the like can be performed.

In the present practical embodiment, the male connector 108 is brought into direct contact with the proximal end tubular part 56 of the valve member 44 so that the valve member 44 is pushed in. However, it may also be acceptable to adopt a structure in which a tubular pusher constituted by a separate member is provided to the proximal end side of the proximal end tubular part, and the valve member is indirectly moved to the distal end side via the pusher.

Additionally, when the valve member 44 moves to the distal end side, the outer circumferential guiding projection 62 provided on the outer circumferential surface 58 of the valve member 44 is guided in contact with the inner circumferential surface 28b of the outer needle hub 18 (large-diameter tube part 22) while the valve member 44 moves to the distal end side. In the present practical embodiment, the inner circumferential surface 28b of the large-diameter tube part 22 has a generally constant inside diameter dimension or has a tapered surface shape whose inside diameter dimension gradually decreases toward the distal end side. Since the outer circumferential guiding projection 62 is compressed to the radially inner side by the inner circumferential surface 28b before movement of the valve member 44 to the distal end side, the outer circumferential guiding projection 62 is compressed to the radially inner side by the inner circumferential surface 28b even after the valve member 44 moves to the distal end side.

Moreover, before the male connector 108 is connected, the inner circumferential surface 66 of the annular sealing projection 64 of the distal end tubular part 52 of the valve member 44 is in close contact with the protruding tip end side of the straight part 38c of the tubular protrusion 38 (axially proximal end side). However, due to the connection of the male connector 108, the valve member 44 moves to the distal end side while the inner circumferential surface 66 of the annular sealing projection 64 is guided in contact with the outer circumferential surface 42 of the tubular protrusion 38. By so doing, after the male connector 108 is connected, the annular sealing projection 64 moves to the distal end side, and the inner circumferential surface 66 thereof comes into close contact with the protruding base end side (axially distal end side) of the straight part 38c. Therefore, in the present practical embodiment, the inner circumferential surface 66 of the annular sealing projection 64 constituting the inner circumferential surface 60a of the distal end tubular part 52 comprises a guide surface that is in contact with the outer circumferential surface 42 of the tubular protrusion 38 so as to guide the movement of the valve member 44.

With the outer needle (valved needle assembly) 10 and the indwelling needle assembly 14 including the outer needle 10 constituted as described above, since the valve member 44 that is movable in the axial direction within the outer needle hub 18 has a generally sleeve shape in which the distal end tubular part 52 and a proximal end tubular part 56 are provided to the central valve part 46, the valve member 44 is prevented from tilting excessively within the outer needle hub 18. Therefore, the tubular protrusion 38 protruding to the proximal end side within the outer needle hub 18 is more reliably inserted through the central valve part 46, and the slit 48 is stably opened, namely, the inside of the male connector 108 and the outer needle main body 16 can stably communicate with each other.

In particular, the outer circumferential guiding projection 62 projecting from the outer circumferential surface 58 of the valve member 44 is in contact with the inner circumferential surface 28b of the outer needle hub 18, and the inner circumferential surface (guide surface) 66 of the annular sealing projection 64 provided at the distal end of the valve member 44 is in contact with the outer circumferential surface 42 of the tubular protrusion 38. This will further prevent the valve member 44 from tilting, thereby more reliably achieving the movement of the valve member 44 to the distal end side.

Besides, the outer circumferential guiding projection 62 can be utilized as a compressing projection. That is, due to the outer circumferential guiding projection 62 being compressed to the radially inner side by the inner circumferential surface 28b of the outer needle hub 18, prior to the insertion of the male connector 108, the slit 48 can be more stably maintained in the closed state.

Furthermore, the annular sealing projection 64 comprises a clamping fit part and is fitted externally onto the straight part 38c of the tubular protrusion 38 in a compressed state. Thus, the inner circumferential surface 66 of the annular sealing projection 64 and the outer circumferential surface 42c of the straight part 38c comprise as sealing faces, thereby providing a liquid-tight sealing between the annular sealing projection 64 and the tubular protrusion 38. This prevents blood from leaking from between the tubular protrusion 38 and the valve member 44, thereby effectively preventing blood from entering and pooling in the space 68 on the distal end side of the valve member 44 or the like, for example.

In particular, before the connection of the male connector 108, the inner circumferential surface 66 of the annular sealing projection 64 is in close contact with the protruding tip end portion of the straight part 38c of the tubular protrusion 38. Meanwhile, after the connection of the male connector 108, the inner circumferential surface 66 of the annular sealing projection 64 comes into close contact with the protruding base end portion of the straight part 38c. That is, both before and after the connection of the male connector 108, more reliable sealing is provided between the annular sealing projection 64 and the tubular protrusion 38, thereby effectively preventing the leakage of blood or liquid medicine into the inside of the outer needle hub 18. Moreover, after the male connector 108 is connected, the distal side end face 50 of the central valve part 46 also comes into close contact with the straight part 38c of the tubular protrusion 38, so that the sealing can be further improved.

In the present practical embodiment, on the radially outer side of the tubular protrusion 38, since the space 68 is provided on the distal end side of the valve member 44, when moving the valve member 44 to the distal end side, it is also possible to move the entire valve member 44 so as to be pushed into the space 68. In particular, in the present practical embodiment, the concave groove 37 (gap 67) provided on the inner circumferential surface 28b of the outer needle hub 18 constitutes the air vent passage for discharging the air in the space 68 on the distal end side of the valve member 44. This can avoid an increase in resistance feeling when inserting the male connector 108 and moving the valve member 44 to the distal end side.

Figure 5A:
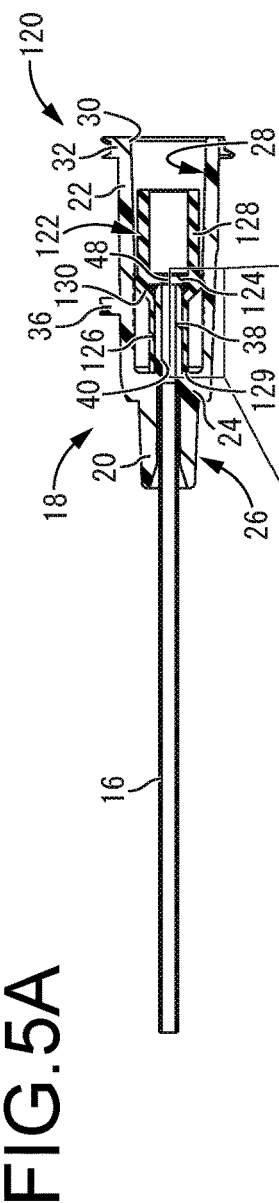
FIG. 5A is a vertical cross sectional view of a valved needle assembly according to a second practical embodiment of the present invention.
Figure 5B:
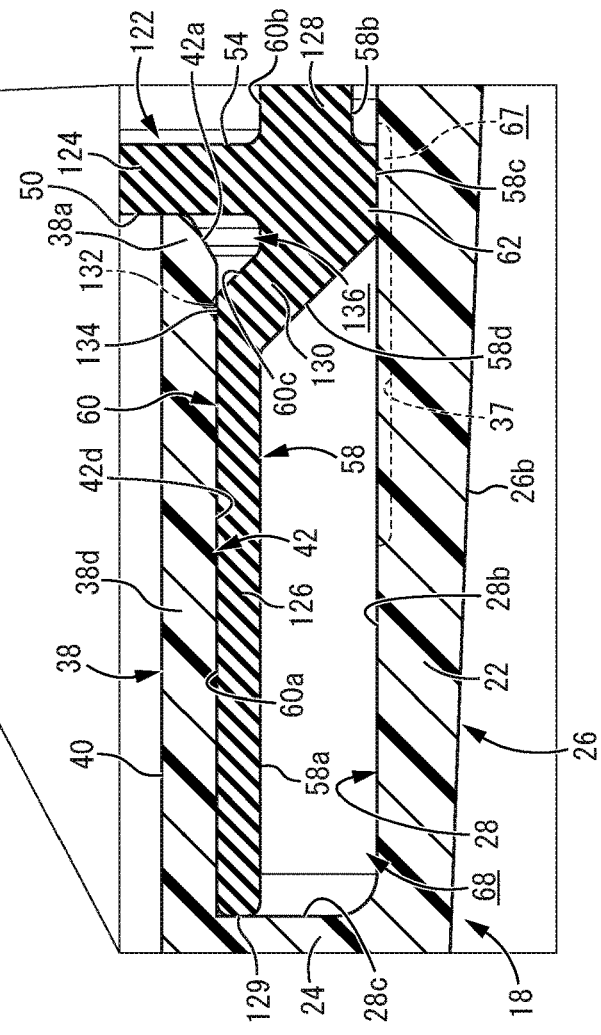
FIG. 5B is an enlarged view of a principal part in FIG. 5A.
Figure 5C:
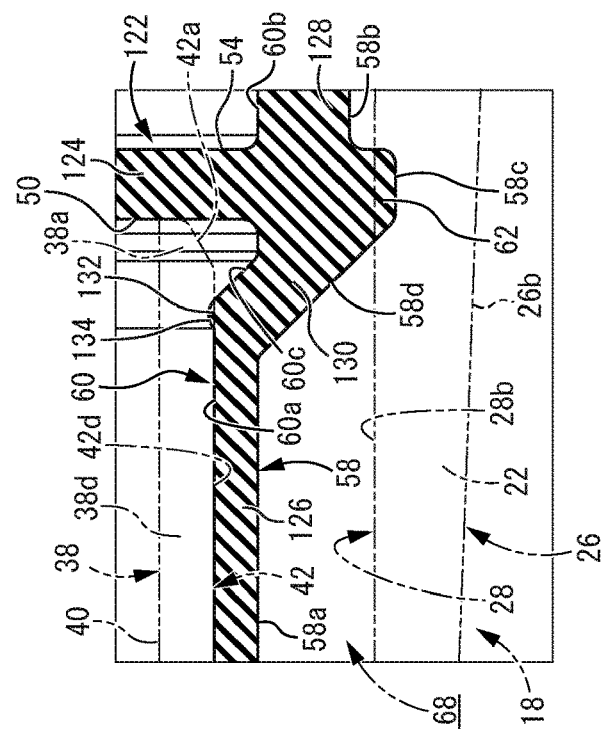
FIG. 5C is an enlarged view of an principal part of a valve member in the isolated state prior to attachment to a needle hub.

Next, FIGS. 5A and 5B depict an outer needle 120 as a second practical embodiment of the valved needle assembly according to the present invention. In the outer needle 120 of the present practical embodiment, a valve member 122 shown in FIG. 5C is attached to the outer needle hub 18 having a structure generally similar to that of the first practical embodiment. Also, in the present practical embodiment, the outer circumferential surface 42a of the axially proximal end section (protruding tip end) 38a of the tubular protrusion 38 has a tapered surface shape (tapered sloping face) that gradually decreases in diameter toward the proximal end side. In addition, the distal end side of the axially proximal end section 38a, namely, the portion from the axially middle section of the tubular protrusion 38 to the axially distal end section (protruding base end) thereof, constitutes a straight part 38d in which the outside diameter dimension of an outer circumferential surface 42d is generally constant. Therefore, in the present practical embodiment, the outside diameter dimension of the tubular protrusion 38 is generally constant across generally the entire length in the axial direction. In the following description, components and parts that are substantially identical with those of the preceding first practical embodiment are denoted by the same reference numerals as those of the preceding first practical embodiment in the drawings, and detailed description thereof is omitted.

Here, the valve member 122 of the present practical embodiment also includes a central valve part 124, a distal end tubular part 126 projecting from the central valve part 124 toward the distal end side, and a proximal end tubular part 128 projecting from the central valve part 124 toward the proximal end side. Also in the present practical embodiment, the distal end tubular part 126 and the proximal end tubular part 128 extend generally straight in the axial direction with a generally constant thickness dimension. That is, the outer circumferential surface 58a and the inner circumferential surface 60a of the distal end tubular part 126 as well as the outer circumferential surface 58b and the inner circumferential surface 60b of the proximal end tubular part 128 each extend in the lengthwise direction (axial direction) with a generally constant diameter dimension. In particular, in the present practical embodiment, the axial dimension of the distal end tubular part 126 is roughly equal to the axial dimension of the tubular protrusion 38 so that the distal end tubular part 126 covers the tubular protrusion 38 as far as the distal end thereof. Thus, in the initial state before the insertion of the male connector 108 as shown in FIGS. 5A and 5B, a distal end face 129 of the distal end tubular part 126 is in contact with the proximal side end face 28c of the intermediate wall 24 of the outer needle hub 18 in the axial direction. The distal end face 129 of the distal end tubular part 126 and the proximal side end face 28c of the intermediate wall 24 may be fixed or do not have to be fixed to each other. Indeed, the distal end face 129 of the distal end tubular part 126 and the proximal side end face 28c of the intermediate wall 24 do not have to be in contact with each other.

The generally annular outer circumferential guiding projection 62 that protrudes to the radially outer side is formed at the outer circumferential end of the central valve part 124. Due to the valve member 122 being attached to the outer needle hub 18, the outer circumferential guiding projection 62 is configured to be compressed to the radially inner side by the inner circumferential surface 28b of the outer needle hub 18 (large-diameter tube part 22). This prevents the valve member 122 from tilting with respect to the outer needle hub 18, as well as the slit 48 is stably closed off. Therefore, in the present practical embodiment as well, the outer circumferential guiding projection 62 constitutes the compressing projection that exerts a compression force in the direction of closing on the slit 48.

Further, as in the first practical embodiment, the proximal end tubular part 128 has an inside diameter dimension larger than the outside diameter dimension of the tubular protrusion 38 (straight part 38d) of the outer needle hub 18, while having the outside diameter dimension smaller than the inside diameter dimension of the large-diameter tube part 22 of the outer needle hub 18. Thus, a generally annular gap is formed radially between the proximal end tubular part 128 and the large-diameter tube part 22 of the outer needle hub 18.

On the other hand, the inside diameter dimension of the distal end tubular part 126 of the present practical embodiment is roughly equal to or slightly larger than the outside diameter dimension of the tubular protrusion 38 (straight part 38d). The outside diameter dimension of the distal end tubular part 126 is not limited in any way, but the distal end tubular part 126 is sufficiently thin so that when moving to the distal end side of the valve member 122 described later, the distal end tubular part 126 readily undergoes elastic deformation. In the present practical embodiment, the distal end tubular part 126 is thinner than the central valve part 124, the proximal end tubular part 128, and a tapered part 130 described later. That is, in the present practical embodiment, the outside diameter dimension of the distal end tubular part 126 is smaller than the outside diameter dimensions of the central valve part 124 and the proximal end tubular part 128, so that the generally annular space 68 is formed radially between the distal end tubular part 126 and the large-diameter tube part 22.

Here, the proximal end portion of the distal end tubular part 126 and the outer circumferential portion of the central valve part 124 are connected by a generally tubular tapered part 130 that gradually decreases in diameter toward the distal end side. That is, an outer circumferential surface 58d of the tapered part 130 that connects the outer circumferential surface 58a of the distal end tubular part 126 and the outer circumferential surface 58c of the central valve part 124 (outer circumferential guiding projection 62) comprises a tapered surface whose outside diameter dimension gradually becomes smaller toward the distal end side. Meanwhile, the inner circumferential surface 60c of the tapered part 130 comprises a tapered surface that gradually decreases in diameter toward the distal end side, and the inner circumferential surface 60c of the tapered part 130 and the distal side end face 50 of the central valve part 124 are connected by an annular surface extending generally parallel to the axial direction.

That is, with the tapered part 130, the outer circumferential surface 58d and the inner circumferential surface 60c both comprise tapered surfaces whose outside diameter dimension and inside diameter dimension respectively decrease gradually toward the distal end side. Thus, the tapered part 130 gradually decreases in diameter from the central valve part 124 toward the distal end tubular part 126, and has a generally constant thickness dimension. On the other hand, with the portion further on the proximal end side than the tapered part 130, the outer circumferential surface 58d comprises a tapered surface while the inside diameter dimension of the inner circumferential surface is generally constant. Thus, the said portion is connected to the central valve part 124 while gradually increasing in thickness dimension toward the proximal end side.

Therefore, in the present practical embodiment, the outer circumferential surface 58 of the valve member 122 includes the outer circumferential surface 58a of the distal end tubular part 126, the outer circumferential surface 58b of the proximal end tubular part 128, the outer circumferential surface 58c of the central valve part 124 (the outer circumferential guiding projection 62), and the outer circumferential surface 58d of the tapered part 130. At the same time, the inner circumferential surface 60 of the valve member 122 includes the inner circumferential surface 60a of the distal end tubular part 126, the inner circumferential surface 60b of the proximal end tubular part 128, and the inner circumferential surface 60c of the tapered part 130.

In particular, in the present practical embodiment, the outer circumferential surface 58d of the tapered part 130 and the distal end surface of the outer circumferential guiding projection 62 have generally the same inclination angle as each other with respect to the axial direction, and these surfaces are formed as one flat tapered surface. By so doing, even when the valve member 122 is moved to the distal end side with the outer circumferential guiding projection 62 compressed to the radially inner side, such as when the valve member 122 is attached to the outer needle hub 18 or when the male connector 108 is inserted, it is possible to avoid increase in friction between the outer circumferential guiding projection 62 and the inner circumferential surface 28b of the outer needle hub 18 (large-diameter tube part 22), thereby facilitating the movement of the valve member 122 to the distal end side.

On the inner circumferential surface 60 of the valve member 122, at the connecting section between the distal end tubular part 126 and the tapered part 130, namely, at the proximal end of the inner circumferential surface 60a of the distal end tubular part 126, or the distal end of the inner circumferential surface 60c of the tapered part 130, there is formed an annular sealing projection 132 projecting radially inward. In the present practical embodiment, the annular sealing projection 132 is formed with a generally semicircular cross section. In the isolated state of the of the valve member 122 before being attached to the outer needle hub 18, the inside diameter dimension at the top of the annular sealing projection 132 is smaller than the outside diameter dimension of the straight part 38d of the tubular protrusion 38 (see FIG. 5C). With this configuration, due to the valve member 122 being attached to the outer needle hub 18, the valve member 122 is pushed to expand radially outward at the formation position of the annular sealing projection 132, and the annular sealing projection 132 is configured to be brought into close contact with the outer circumferential surface 42d of the straight part 38d due to its elastic recovery force. That is, in the present practical embodiment as well, the clamping fit part is constituted by the annular sealing projection 132, and an inner circumferential surface 134 of the annular sealing projection (clamping fit part) 132 comprises the sealing face. Besides, when the valve member 122 moves to the distal end side, which will be described later, the valve member 122 is moved while the inner circumferential surface 134 of the annular sealing projection 132 is in close contact with the outer circumferential surface 42d of the straight part 38d. Thus, also in the present practical embodiment, the guide surface that guides the movement of the valve member 122 toward the distal end side is constituted by the inner circumferential surface 134 of the annular sealing projection 132. However, in the present practical embodiment, roughly the entire surface of the inner circumferential surface 60a of the distal end tubular part 126 touches the outer circumferential surface 42d of the straight part 38d with almost no gap therebetween or is only slightly remote therefrom. Thus, it is also possible to recognize the generally entire surface of the inner circumferential surface 60a of the distal end tubular part 126 as the guide surface that guides the movement of the valve member 122 toward the distal end side.

In the present practical embodiment, in the in the isolated state of the valve member 122, the inside diameter dimension of the distal end tubular part 126 excluding the annular sealing projection 132 is roughly equal to or slightly larger than the outside diameter dimension of the straight part 38d of the tubular protrusion 38. In the attached state of the valve member 122 and the outer needle hub 18, the inner circumferential surface 60a of the distal end tubular part 126 excluding the annular sealing projection 132 and the outer circumferential surface 42d of the straight part 38d touch with almost no gap therebetween or are slightly remote with respect to each other across generally the entire length in the axial direction. That is, in the present practical embodiment, the sealing face is constituted only by the inner circumferential surface 134 of the annular sealing projection 132 on the inner circumferential surface 60a of the distal end tubular part 126, and the portion that does not constitute the sealing face is formed with an axial dimension longer than that of the portion that constitutes the sealing face.

The inner circumferential surface 60c of the tapered part 130 comprises a tapered surface whose inside diameter dimension gradually decreases toward the distal end side. Accordingly, with the valve member 122 attached to the outer needle hub 18, an annular gap 136 is formed on the radially inner side of the tapered part 130, namely, radially between the tapered part 130 and the tubular protrusion 38. That is, the annular gap 136 is formed in a region surrounded by the tapered part 130, the tubular protrusion 38, and the central valve part 124. In the present practical embodiment, when the valve member 122 and the outer needle hub 18 are attached, the protruding tip end face of the tubular protrusion 38 and the distal side end face 50 of the central valve part 124 are in contact with each other, so that the gap 136 and the space inside the tubular protrusion 38 (center hole 40) do not communicate with each other. However, it would also be acceptable that the protruding tip end face of the tubular protrusion 38 and the distal side end face 50 of the central valve part 124 are not in contact with each other so that the gap 136 and the space inside the tubular protrusion 38 (center hole 40) communicate with each other.

Figure 6:
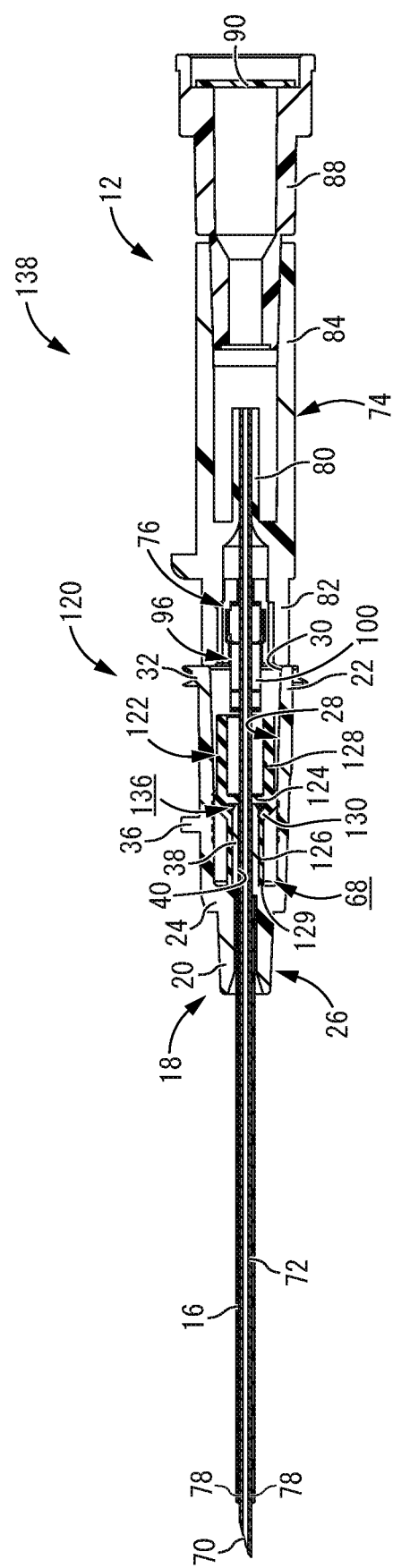
FIG. 6 is a vertical cross sectional view of an indwelling needle assembly including the valved needle assembly shown in FIGS. 5A-5C.

By inserting the valve member 122 having such a structure from the proximal end opening part 30 of the outer needle hub 18 and inserting the tubular protrusion 38 into the distal end tubular part 126, the valve member 122 is attached to the outer needle hub 18 including the outer needle main body 16, thereby providing the outer needle 120 of the present practical embodiment. In particular, in the present practical embodiment, the annular sealing projection 132 that is in close contact with the outer circumferential surface 42 (42d) of the tubular protrusion 38 (straight part 38d) is formed only at the proximal end portion of the distal end tubular part 126. Therefore, when inserting the tubular protrusion 38 into the distal end tubular part 126, the distal end tubular part 126 will be effectively prevented from deforming, for example, in a corrugated shape in the axial direction, thereby obtaining good assembly workability. Then, by the inner needle 12 having the same structure as that of the first practical embodiment being attached to the outer needle 120, an indwelling needle assembly 138 is constituted as shown in FIG. 6.

Figure 7:
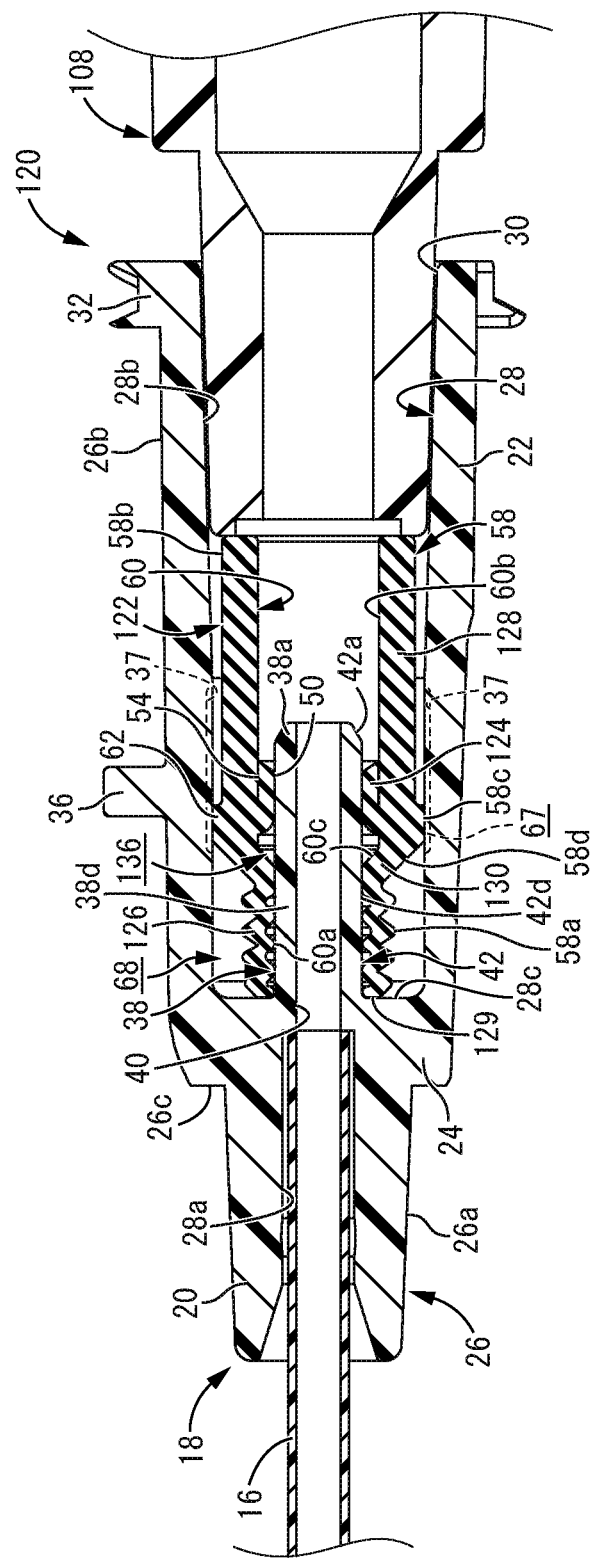
FIG. 7 is an enlarged vertical cross sectional view of the valved needle assembly shown in FIGS. 5A-5C with a male connector inserted.

By sticking the indwelling needle assembly 138 into the skin and removing the inner needle 12, the outer needle 120 is indwelled in the skin of the patient. Then, as shown in FIG. 7, by inserting the male connector 108 such as a syringe from the proximal end opening part 30 of the outer needle 120, the valve member 122 is pushed to the distal end side by the distal end of the male connector 108, and the slit 48 is pushed open by the tubular protrusion 38, thereby making it possible to perform infusion, blood transfusion, blood collection, or the like. Besides, in the present practical embodiment as well, the wall parts on both sides of the slit 48 in the central valve part 124 are deformed so as to bend to the proximal end side, and the distal side end face 50 of the central valve part 124 comes into close contact with the outer circumferential surface 42d of the straight part 38d of the tubular protrusion 38.

Here, as shown also in FIG. 5 and the like, at the time before the male connector 108 is inserted and the valve member 122 moves to the distal end side, the distal end face 129 of the distal end tubular part 126 is in contact with the proximal side end face 28c of the intermediate wall 24. Thus, due to the male connector 108 being inserted and the central valve part 124 of the valve member 122 moving toward the distal end side, namely, toward the tubular protrusion 38, the distal end tubular part 126 is compressed between the central valve part 124 and the intermediate wall 24 in the axial direction so as to be elastically deformed. By so doing, in the present practical embodiment, as shown in FIG. 7, the distal end tubular part 126 elastically deforms in a corrugated shape in the lengthwise direction, or in a bellows shape, that is, a shape in which peaks and valleys are alternately continuous in the axial direction, so that the axial dimension of the distal end tubular part 126 is shortened in comparison with the state before the male connector 108 is inserted. The elastic deformation of the distal end tubular part 126 configured to occur in the portion that does not constitute the sealing face in the distal end tubular part 126, namely, on the distal end side of the annular sealing projection 132. Therefore, elastic deformation does not occur in the portion that constitutes the sealing face in the distal end tubular part 126 (annular sealing projection 132), and even in the case where the valve member 122 moves to the distal end side as described above and the distal end tubular part 126 is elastically deformed, the seal of the outer circumferential surface 42d of the tubular protrusion 38 (straight part 38d) by means of the annular sealing projection 132 can be maintained.

With the outer needle (valved needle assembly) 120 and the indwelling needle assembly 138 having the outer needle 120 structured as described above as well, the same effects as those in the first practical embodiment can be obtained. In particular, in the present practical embodiment, the distal end tubular part 126 covers the tubular protrusion 38 across generally the entire length in the axial direction, thereby more reliably preventing the valve member 122 from tilting with respect to the outer needle hub 18.

Besides, in the present practical embodiment, the annular gap 136 is formed between the annular sealing projection 132 and the central valve part 124 in the axial direction. By providing such a gap 136, even in the case where the male connector 108 is inserted into the outer needle hub 18 and the wall parts on both sides of the slit 48 in the central valve part 124 are deformed by the tubular protrusion 38 so as to bend to the proximal end side, the force accompanying the deformation will not be directly exerted on the annular sealing projection 132, and the seal of the outer circumferential surface 42 of the tubular protrusion 38 by means of the annular sealing projection 132 will be stably maintained. In other words, by providing the gap 136, the slit 48 can be stably pushed open by the tubular protrusion 38 with the seal by the annular sealing projection 132 maintained.

Further, in the present practical embodiment, the tapered part 130 is thicker than the distal end tubular part 126, and the annular sealing projection 132 is provided at the connecting section between the tapered part 130 and the distal end tubular part 126. That is, the annular sealing projection 132 is provided at a portion that is thicker than the other portions of the distal end tubular part 126 and is less likely to undergo elastic deformation. Accordingly, it is possible to readily cause elastic deformation of the distal end tubular part 126 excluding the annular sealing projection 132 while stably maintaining the seal of the outer circumferential surface 42 of the tubular protrusion 38 while easily causing the elastic deformation of the tubular protrusion 38. In addition, since the portion further on the proximal end side than the tapered part 130 is connected to the central valve part 124 while gradually becoming thicker toward the proximal end side (the central valve part 124 side), the shape of the outer circumferential portion of the central valve part 124 can be stably maintained. This makes it possible to more effectively obtain the guide action by the outer circumferential guiding projection (compressing projection) 62 provided on the outer circumferential portion of the central valve part 124 and the closing-off action of the slit 48.

In particular, by providing such an annular sealing projection 132, leakage of blood or liquid medicine will be more reliably prevented when puncturing the skin or inserting the male connector 108. Further, even when a space is formed radially between the distal end tubular part 126 and the tubular protrusion 38, the space will not communicate with the gap 136 formed radially between the tapered part 130 and the tubular protrusion 38, and the volume of the gap 136 can be made as small as possible. Accordingly, even when air remains in the gap 136 when the valve member 122 and the outer needle hub 18 are attached, the amount of air mixed into the body of the patient through the outer needle 120 can be minimized.

Furthermore, in the present practical embodiment, when the male connector 108 is inserted and the valve member 122 is moved to the distal end side, the distal end tubular part 126 is configured to be compressed in the axial direction and deformed. That is, when the male connector 108 is inserted, the urging force toward the proximal end side is exerted on the proximal end tubular part 128 by the elastic recovery force of the distal end tubular part 126. Thus, communication (connection) between the proximal end tubular part 128 and the male connector 108 can be stably maintained. Note that, when the male connector 108 is removed, by utilizing the elastic recovery force, the central valve part 124 can be displaced to the initial position by the elastic recovery force of the distal end tubular part 126, so that the slit 48 can be closed off with the removal of the male connector 108. By so doing, the male connector 108 can be inserted into and removed from the outer needle (valved needle assembly) 120 a plurality of times. In particular, the distal end tubular part 126 is thinner than the tapered part 130, the central valve part 124, and the proximal end tubular part 128, thereby easily undergoing the elastic deformation.

Next, FIGS. 8A and 8B depict an outer needle (a valved needle assembly) 140 as another mode of the present practical embodiment. That is, in a valve member 142 in this mode, the distal end tubular part 126 covers the tubular protrusion 38 as far as the distal end thereof and extends as far as the distal end of the inside of the outer needle hub 18. In addition, as shown in FIG. 8C, an annular sealing projection 144 is provided at the distal end portion of the inner circumferential surface 60a of the distal end tubular part 126. In the isolated state of the valve member 142 before being attached to the outer needle hub 18, the inside diameter dimension of the annular sealing projection 144 is smaller than the outside diameter dimension of the straight part 38d of the tubular protrusion 38 (see FIG. 8C). However, by the valve member 142 being attached to the outer needle hub 18, the annular sealing projection 144 is pushed to expand radially outward by the outer circumferential surface 42d of the straight part 38d, so that the annular sealing projection 144 is brought into close contact with the outer circumferential surface 42d of the straight part 38d due to its elastic recovery force.

On the other hand, in the portion of the distal end tubular part 126 that is away from the annular sealing projection 144, the outer circumferential surface 42 of the tubular protrusion 38 touches the inner circumferential surface 60a of the distal end tubular part 126 with roughly almost no gap therebetween or is slightly remote therefrom. That is, in this mode as well, the inner circumferential surface 146 of the annular sealing projection 144 comprises the sealing face. Besides, the portion that does not constitute the sealing face in the inner circumferential surface 60a of the distal end tubular part 126 is formed with an axial dimension longer than the portion that constitutes the sealing face (annular sealing projection 144). Further, in this mode as well, it is also possible to recognize the generally entire surface of the inner circumferential surface 60a of the distal end tubular part 126 as the guide surface.

In the present practical embodiment, the valve member 142 is not provided with the tapered part (130), and the gap (136) is not formed between the tubular protrusion 38 and the valve member 142 either. Instead of such a structure, in this mode, at the connecting section between the distal end tubular part 126 and the central valve part 124 (proximal end part of the distal end tubular part 126), there is provided an overlapping part 148 serving as the connecting part that is overlapped with the outer circumferential surface 42a of the protruding tip end (axially proximal end section) 38a of the tubular protrusion 38. That is, since the outer circumferential surface 42a of the protruding tip end 38a of the tubular protrusion 38 comprises a tapered sloping face that gradually decreases in diameter toward the central valve part 124, the overlapping part 148 has a sloping inner face 150 that gradually decreases in diameter toward the central valve part 124 so as to correspond to the tapered sloping face 42a. In other words, the overlapping part 148 is configured such that the thickness dimension (axis-perpendicular dimension) gradually increases from the distal end tubular part 126 toward the central valve part 124.

The valve member 142 having the above-described structure is attached to the outer needle hub 18, so that the outer circumferential surface (tapered sloping face) 42a of the protruding tip end 38a of the tubular protrusion 38 and the sloping inner face 150 of the overlapping part 148 are brought into contact and overlapped with each other. By so doing, the outer circumferential surface 42 of the tubular protrusion 38 is overlapped with the inner circumferential surface 60a of the distal end tubular part 126 with generally no gap over roughly the entire surface. This makes it possible to reduce the risk of air remaining in the space between the tubular protrusion 38 and the distal end tubular part 126, thereby effectively preventing the air from entering the body of the patient.

Also in this mode, the annular sealing projection 144 is formed so as to provide a seal between the tubular protrusion 38 and the distal end tubular part 126, thereby effectively preventing leakage of blood and liquid medicine through the space between the tubular protrusion 38 and the distal end tubular part 126. In particular, also in this mode, the distal end tubular part 126 covers the tubular protrusion 38 across generally the entire length in the axial direction, and the annular sealing projection 144 at the distal end portion of the distal end tubular part 126 is configured to be in close contact and seal with respect to the outer circumferential surface at the distal end portion of the tubular protrusion 38 (distal end outer circumferential surface 42e) about the entire circumference. In the present practical embodiment as well, by inserting the male connector (108) and moving the valve member 142 toward the distal end side, the distal end tubular part 126 is configured to be compressed in the axial direction, and as in the preceding mode shown in FIGS. 5A to 7, the portion that does not constitute the sealing face (the portion where the annular sealing projection 144 is not formed) on the inner circumferential surface 60a of the distal end tubular part 126 is configured to be elastically deformed in a corrugated shape, for example, in the axial direction. That is, in this mode, the distal end tubular part 126 is in contact with only the distal end outer circumferential surface 42e of the tubular protrusion 38 about the entire circumference in a compressed state. Due to the proximal end tubular part 128 being pressed to the distal end side by the male connector (108) serving as an external instrument, the lengthwise middle portion of the distal end tubular part 126 is configured to elastically deform in the radial direction. Also, in this mode as well, since the distal end tubular part 126 is thinner than the central valve part 124 and the proximal end tubular part 128, such elastic deformation can be easily induced.

Figure 9A:
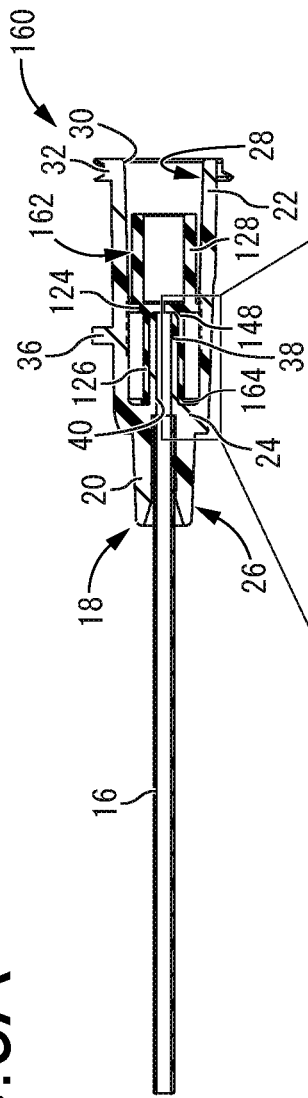
FIG. 9A is a vertical cross sectional view showing yet another practical embodiment of the valved needle assembly shown in FIGS. 5A-5C.
Figure 9B:
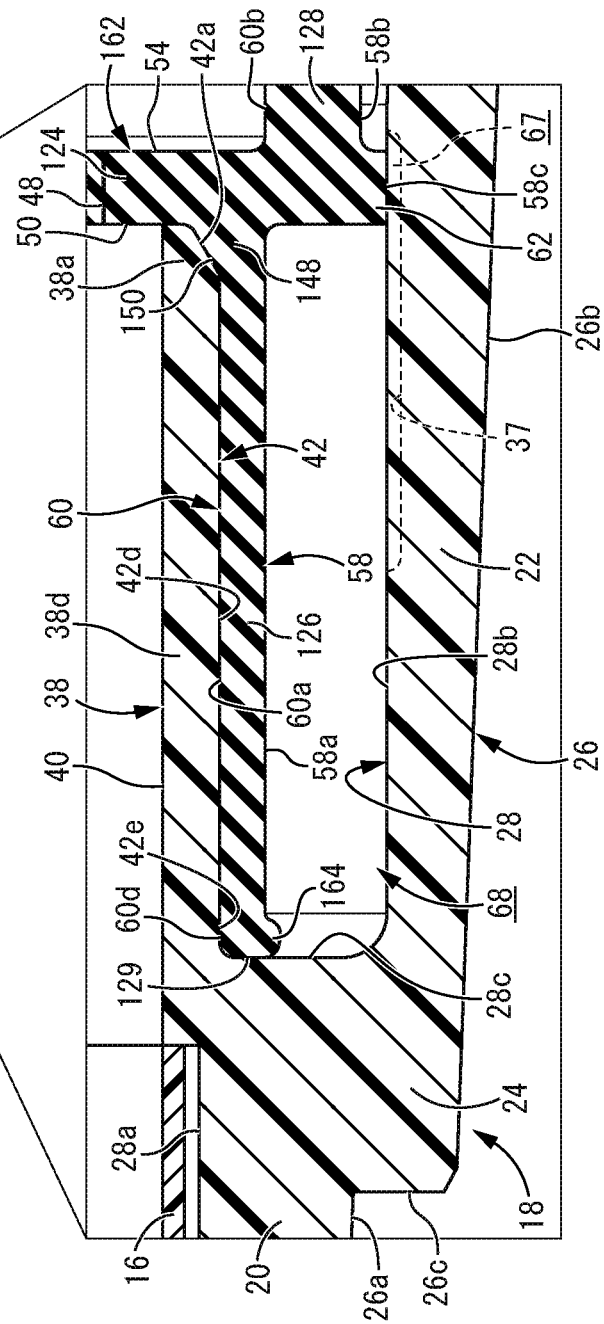
FIG. 9B is an enlarged view of a principal part in FIG. 9A.

Furthermore, FIGS. 9A and 9B depict an outer needle (valved needle assembly) 160 as still another mode of the present practical embodiment. In this mode, in a valve member 162 in the isolated state before being attached to the outer needle hub 18, the axial dimension of the distal end tubular part 126 is slightly larger than the axial dimension of the tubular protrusion 38. Due to the valve member 162 being attached to the outer needle hub 18, the distal end tubular part 126 covers the tubular protrusion 38 as far as the distal end thereof and extends as far as the distal end of the inside of the outer needle hub 18. At the same time, the distal end tubular part 126 is slightly compressed in the axial direction, and the distal end face 129 of the distal end tubular part 126 and the proximal side end face 28c of the intermediate wall 24 are in close contact with each other in the axial direction. In other words, in this mode, the distal end face 129 of the distal end tubular part 126 comprise the sealing face, and blood or liquid medicine is prevented from leaking through a gap between the distal end tubular part 126 and the tubular protrusion 38 by the seal by the sealing face. Therefore, the portion sealed by the sealing face is not only the outer circumferential surface 42 of the tubular protrusion 38, but may also be the proximal side end face 28c of the intermediate wall 24 continuous from the outer circumferential surface 42 of the tubular protrusion 38 or the inner circumferential surface 28b of the large-diameter tube part 22.

Note that, by the distal end tubular part 126 being compressed in the axial direction, the urging force toward the proximal end side is exerted on the central valve part 124 and the proximal end tubular part 128 due to elastic recovering deformation of the distal end tubular part 126. However, the outer circumferential guiding projection 62 provided on the radially outer side of the central valve part 124 is attached in a compressed state with respect to the outer needle hub 18, thereby preventing the movement of the central valve part 124 and the proximal end tubular part 128 to the proximal end side. That is, due to the pressing reaction force of the outer circumferential guiding projection 62 being exerted on the inner circumferential surface 28b of the outer needle hub 18 (large-diameter tube part 22), the valve member 162 is positioned in the axial direction with respect to the outer needle hub 18, so that the distal end tubular part 126 is attached in a state of being compressed in the axial direction. However, for example, it would also be possible to separately provide a mechanism for preventing the movement of the central valve part 124 and the proximal end tubular part 128 to the proximal end side without providing the outer circumferential guiding projection 62, or even in the case where the outer circumferential guiding projection 62 is provided.

With the valve member 162 attached to the outer needle hub 18, the inner circumferential surface 60a of the distal end tubular part 126 and the outer circumferential surface 42 of the tubular protrusion 38 may touch each other with almost no gap therebetween, or may be slightly remote with respect to each other. Therefore, also in this mode, it is also possible to recognize the generally entire surface of the inner circumferential surface 60a of the distal end tubular part 126 as the guide surface.

Here, a flanged part 164 that projects to the radially outer side is formed at the distal end of the distal end tubular part 126 of this mode, so that the area of the distal end face 129 of the distal end tubular part 126 is increased. In this mode, the projecting dimension of the flanged part 164 to the radially outer side is not large enough to reach the inner circumferential surface 28b of the large-diameter tube part 22 of the outer needle hub 18. However, the outer circumferential surface of the flanged part 164 may be in contact with the inner circumferential surface 28b of the large-diameter tube part 22, that is, the distal end face 129 of the distal end tubular part 126 and the proximal side end face 28c of the intermediate wall 24 may be in close contact with each other over generally the entire face.

By providing the flanged part 164, the contact area between the distal end face 129 and the proximal side end face 28c is increased, so that the sealing effect by the distal end face 129 of the distal end tubular part 126 can be stably exhibited. It would also be acceptable that, by the distal end tubular part 126 being compressed in the axial direction, the inner circumferential surface 60a of the distal end tubular part 126 undergoes swelling deformation to the radially inner side so as to come into close contact with the outer circumferential surface 42 of the tubular protrusion 38. For example, a distal end 60d of the inner circumferential surface 60a of the distal end tubular part 126 (for example, the inner circumferential surface of the flanged part 164) may undergo swelling deformation to the radially inner side, so as to come into close contact with the tubular protrusion 38 (38d) may be in close contact with the distal end outer circumferential surface 42e of the tubular protrusion 38 (38d) about the entire circumference in the circumferential direction. That is, the sealing face may also be constituted by the distal end 60d of the inner circumferential surface 60a, for example, in addition to the distal end face 129 of the distal end tubular part 126. However, the portion of the inner circumferential surface 60a of the distal end tubular part 126 that undergoes the swelling deformation to the radially inner side is not limited to the distal end 60d, but may be the axially middle portion or the axially proximal end portion. Thus, the sealing face may be constituted by the axially middle portion or the axially proximal end portion of the inner circumferential surface 60a. Also in this mode, since the distal end tubular part 126 is thinner than the central valve part 124 and the proximal end tubular part 128, elastic deformation of the distal end tubular part 126 can be easily induced.

The valve member 162 may be molded in a state where the flanged part 164 is provided at the distal end of the distal end tubular part 126 in the isolated state before the valve member 162 is attached to the outer needle hub 18. However, the distal end tubular part 126 of the valve member 162 may alternatively be molded in a state of extending in a generally straight line in the axial direction without the flanged part 164 being provided. In such a case, it would also be acceptable that, by the valve member 162 being attached to the outer needle hub 18, the distal end tubular part 126 is compressed in the axial direction, and the distal end of the distal end tubular part 126 undergoes swelling deformation to the radially outer side so as to form the flanged part 164.

With the outer needle (valved needle assembly) 160 having such a structure as well, by inserting the male connector (108) and moving the valve member 162 to the distal end side, as in the preceding mode shown in FIGS. 5A to 7, for example, the distal end tubular part 126 is configured to be elastically deformed in a corrugated shape in the axial direction. That is, due to the proximal end tubular part 128 being pressed to the distal end side by the male connector (108) serving as the external instrument, for example, the lengthwise middle portion of the distal end tubular part 126, where the sealing face is not formed on the inner circumferential surface 60a of the distal end tubular part 126, for example, is configured to deform in the radial direction, namely, to elastically deform in a corrugated shape in the axial direction, for example.

In the present practical embodiment, in the initial state, the distal end face 129 of the distal end tubular part 126 and the proximal side end face 28c of the intermediate wall 24 do not need to be in contact (close contact) with each other. Thus, it would also be acceptable that, due to the movement of the valve member 162 accompanying the insertion of the male connector (108), the distal end face 129 of the distal end tubular part 126 and the proximal side end face 28c of the intermediate wall 24 come into close contact with each other and provide the seal therebetween. That is, in this mode, in the initial state for example, only the distal end outer circumferential surface 42e may be sealed by the distal end 60d of the distal end tubular part 126 with or without providing the annular sealing projection (144) as described in the mode shown in FIGS. 8A and 8B. Then, by inserting the male connector (108) serving as the external instrument, in addition to the distal end outer circumferential surface 42e, the proximal side end face 28c of the intermediate wall 24 may be sealed.

While the present invention has been described hereinabove in terms of certain practical embodiments, these are merely exemplary, and the invention shall not be construed as limited in any way to the specific disclosures in the practical embodiments.

For example, in the valved needle assembly according to the present invention, it would also be acceptable to provide a returning means for exerting an operating force on the valve member in the direction of returning to the original position before the movement when the male connector is inserted into the outer needle to open the slit and then the male connector is removed from the outer needle. Such a returning means is not limited in any way, but for example, the valve member may be configured to be returned to the original position by the elastic recovery force of the central valve part bent toward the proximal end side due to the movement of the valve member toward the distal end side, namely, the returning means may be constituted by including the bent central valve part. By so doing, when the male connector is removed from the outer needle, it is possible to return the valve member to the original position, and have the central valve part recover the original shape, thereby placing the slit in the closed state again. By providing such a return means, for example, when the infusion is interrupted or the like, the male connector is temporarily removed to block communication with the hollow needle, and when the infusion is resumed, the male connector is inserted again so as to place the hollow needle and the male connector in communication or the like, so that the male connector can be connected to the outer needle a plurality of times.

Besides, in the preceding first practical embodiment, the entire valve member 44 moves to the distal end side due to the insertion of the male connector 108. However, it would be acceptable as long as at least the central valve part moves to the distal end side and the slit is opened by the protrusion. That is, as described in, for example, the preceding second practical embodiment and Japanese Unexamined Patent Publication No. JP-A-2004-242763, the distal end tubular part may be compressed in the axial direction by the movement of the central valve part toward the distal end side due to the insertion of the male connector. In such a case, due to the male connector being removed, the distal end tubular part may be elastically undergo recovering deformation so that the valve member returns to the original position, and the aforementioned returning means may be constituted by including the distal end tubular part. In addition, as described in Japanese Unexamined Patent Publication No. JP-A-2004-242763, the distal end tubular part of the valve member may be fixed to the inner circumferential surface of the needle hub or the outer circumferential surface of the protrusion.

Furthermore, the returning means for returning the valve member to the original position may be configured such that, for example, the outer circumferential surface of the protrusion or the inner circumferential surface of the needle hub comprises a tapered surface shape, and the valve member returns to the original position by sliding with respect to the tapered surface, in addition to utilizing the elasticity of the valve member as described above. Besides, it would also be acceptable to provide, for example, an elastic member such as a coil spring that exerts an urging force in a direction returning to the original position on the valve member during insertion of the male connector between the needle hub and the valve member, and due to the removal of the male connector, the valve member is configured to return to the original position in accordance with the urging force. Moreover, it would also be acceptable to make the space on the distal end side or the radially outer side of the distal end tubular part of the valve member a sealed space, and when the valve member moves to the distal end side, the air in the space on the distal end side or the radially outer side of the distal end tubular part is compressed, so as to apply the returning force to the valve member in the direction toward the proximal end. With respect to these returning means, one of them may be adopted, for example, or a plurality of them may be adopted in combination. Indeed, the returning means is not essential, and after completion of the infusion or the like, the outer needle (valved needle assembly) may be removed and discarded together with the male connector.

Further, whereas in the preceding practical embodiment, the protrusion extending to the proximal end side inside the outer hub 18 has a tubular shape, the present invention is not limited to this mode. That is, the protrusion may extend in the axial direction with, for example, an arcuate cross section. Alternatively, if there is separately provided a communication hole for placing the large-diameter tube part 22 of the outer needle hub 18 and the small-diameter tube part 20 (outer needle main body 16, which is a hollow needle) in communication, the protrusion may have, for example, an elongated block shape. In this case, the protrusion may have various types of cross sectional shapes such as a circular cross section including an oval, an ellipse, and semicircle, and a polygonal cross section.

Moreover, in the preceding first practical embodiment, with respect to the outer circumferential surface 42 of the tubular protrusion 38, the outer circumferential surface 42*a* of the axially proximal end section 38*a* and the outer circumferential surface 42*b* of the axially distal end section 38*b* comprise a tapered surface shape, while the axially middle section comprise the straight part 38*c* having a generally constant outside diameter dimension. Also, in the preceding second practical embodiment, only the outer circumferential surface 42*a* of the axially proximal end section 38*a* comprises a tapered surface shape, and the axially distal end section and the axially middle section comprise the straight part 38*d*. However, the present invention is not limited to these modes. That is, the protrusion may have a straight shape across the entire length without providing a tapered portion on the outer circumferential surface, or may alternatively have a tapered shape across the entire length without providing a straight portion. Besides, even in the case where the tapered portion and the straight portion are provided, their formation positions are not limited in any way. Namely, the straight portion may be provided to the axially proximal end section or the axially distal end section, or the tapered portion may be provided to the axially middle section. Note that in the preceding practical embodiments, the axially middle section of the tubular protrusion 38 comprises the straight part 38*c*, 38*d* across the entire length. However, the present invention is not limited to these modes, but it is preferable that at least a part of the axially middle section comprises the straight part.

Additionally, in the preceding practical embodiments, the outer circumferential guiding projection (compressing projection 62) and the annular sealing projection (clamping fit part) 64, 132, 144 have an annular shape extending continuously about the entire circumference in the circumferential direction. However, the present invention is not limited to these modes. That is, one or a plurality of the outer circumferential guiding projections (compressing projections 62) and the clamping fit parts may be formed partially in the circumferential direction. Besides, the outer circumferential guiding projection (compressing projection) do not have to be provided at the outer circumferential end of the central valve part, but may be provided on the distal end tubular part or the proximal end tubular part. Further, the annular sealing projection (clamping fit part) does not have to be provided at the distal end portion of the distal end tubular part as in the first practical embodiment or the mode shown in FIGS. 8A to 8C, but may be provided at the proximal end portion of the distal end tubular part as in the second practical embodiment (the mode shown in FIGS. 5A to 7) or at the axially middle portion of the distal end tubular part.

In the preceding practical embodiment, the outer circumferential guiding projection (compressing projection) 62 projects from the outer circumferential surface 58 of the valve member 44, 122, 142, 162 to the radially outer side. However, the outer circumferential guiding projection and the compressing projection may project from the inner circumferential surface of the needle hub to the radially inner side. Similarly, in the preceding practical embodiments, the annular sealing projection (clamping fit part) 64, 132, 144 projects from the inner circumferential surface 60*a* of the distal end tubular part 52, 126 to the radially inner side. However, it would also be acceptable to provide a projection projecting to the radially outer side from the outer circumferential surface of the protrusion that protrudes toward the proximal end side inside the needle hub so as to exhibit a sealing effect or the like.

Figure 10:
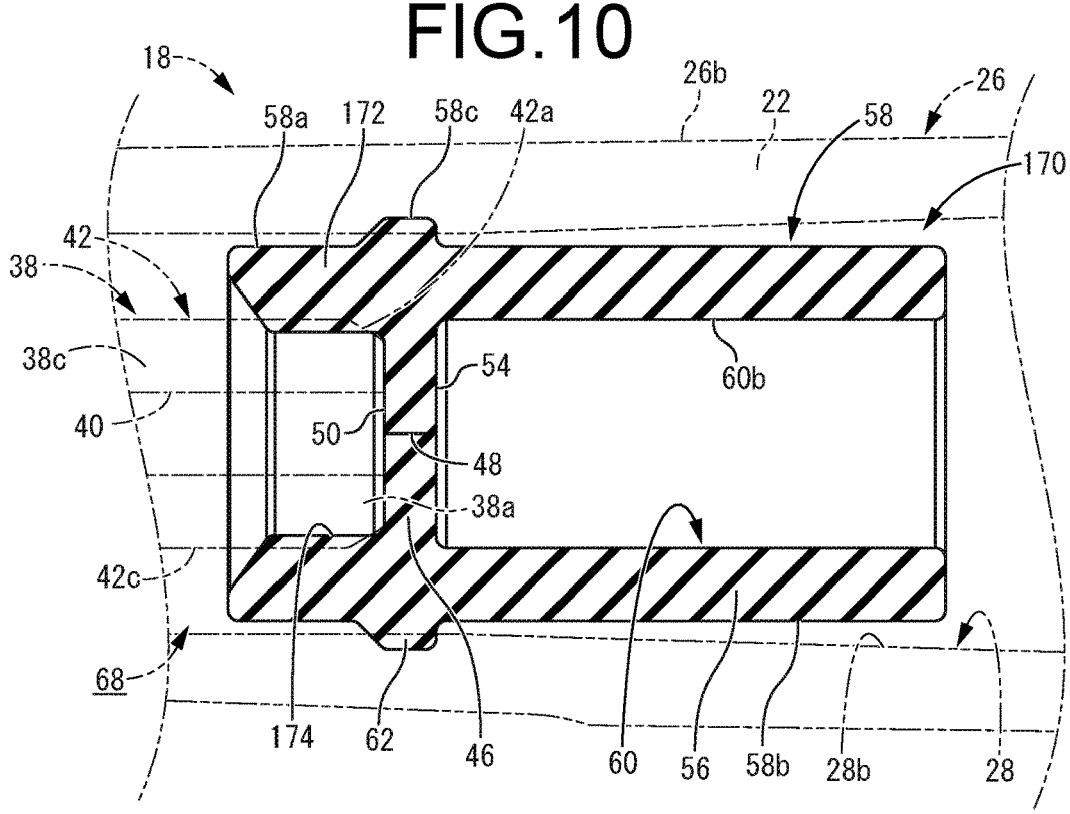
FIG. 10 is an enlarged vertical cross sectional view of a valve member in the isolated state constituting a valved needle assembly according to a further practical embodiment of the present invention.

In the preceding practical embodiments, the clamping fit part is constituted by the annular sealing projection 64, 132, 144. However, the clamping fit part may be constituted without providing the annular sealing projection. That is, in a valve member 170 shown in FIG. 10 in the isolated state before being attached to the outer needle hub 18, no annular sealing projection (64, 132, 144) as described in the preceding practical embodiments is formed on an inner circumferential surface 174 of a distal end tubular part 172. Therefore, the distal end tubular part 172 is a tubular part whose inner circumferential surface 174 extends generally straight. The inside diameter dimension of the distal end tubular part 172 in such an isolated state is smaller than the outside diameter dimension of the straight part 38*c* of the tubular protrusion 38 provided to the outer needle hub 18. Thus, with the valve member 170 attached to the outer needle hub 18, the inner circumferential surface 174 of the distal end tubular part 172 is fitted externally in an expanded state of being pushed open to the radially outer side by the tubular protrusion 38. In other words, the distal end tubular part 172 tightens the tubular protrusion 38 from the radially outer side, and the inner circumferential surface 174 of the distal end tubular part 172 is in contact with the outer circumferential surface 42*c* of the straight part 38*c* of the tubular protrusion 38, so as to exhibit sealing between the valve member 170 and the outer needle hub 18. That is, in this mode, the clamping fit part is constituted by the distal end tubular part 172, and the sealing face is constituted by the inner circumferential surface 174 of the distal end tubular part 172. In addition, a guide surface that guides the movement of the valve member 170 toward the distal end side can be constituted by the inner circumferential surface 174 of the distal end tubular part 172.

Figure 11:
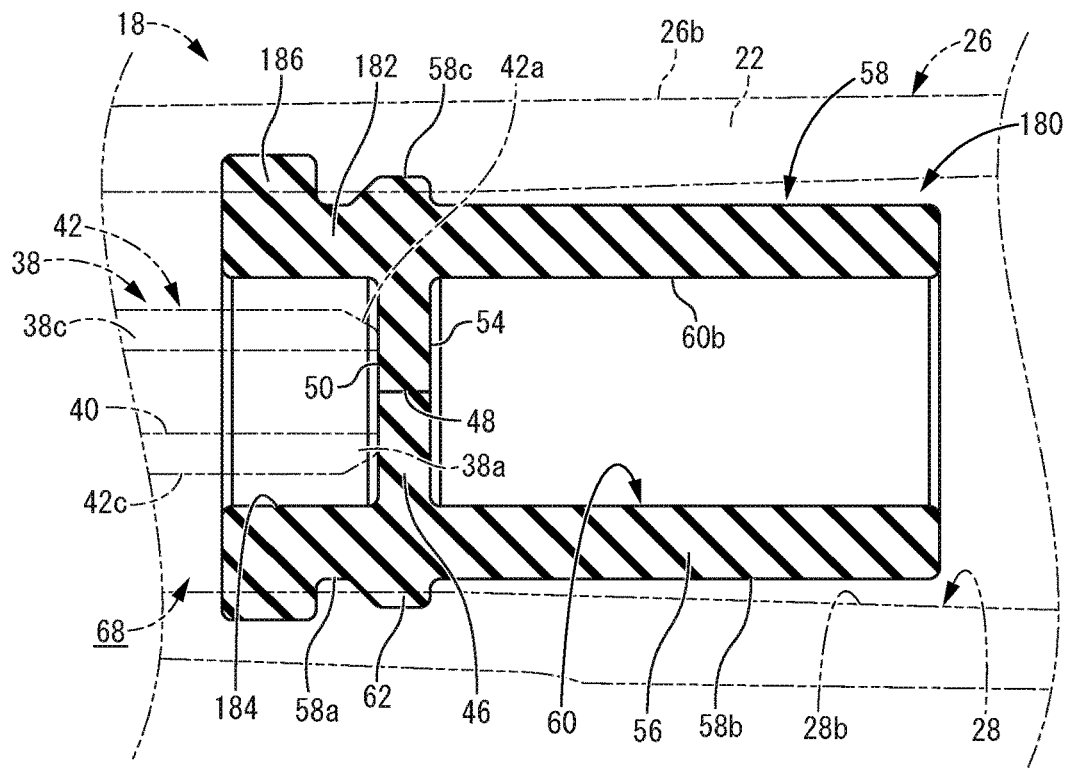
FIG. 11 is an enlarged vertical cross sectional view of a valve member in the isolated state constituting a valved needle assembly according to a yet further practical embodiment of the present invention.

In the mode shown in FIG. 11 as well, the inner circumferential surface of the distal end tubular part may comprise the sealing face. That is, FIG. 11 depicts a valve member 180 in the isolated state before being attached to the outer needle hub 18, and in this mode as well, the annular sealing projection (64, 132, 144) as in the preceding practical embodiments is not provided on an inner circumferential surface 184 of a distal end tubular part 182. On the other hand in this mode, at the distal end portion of the outer circumferential surface 58*a* of the distal end tubular part 182, there is provided a pressing projection 186 that projects to the radially outer side. The pressing projection 186 has an annular shape extending continuously about the entire circumference in the circumferential direction, and its outside diameter dimension in the isolated state is larger than the inside diameter dimension of the outer needle hub 18. With this configuration, by attaching the valve member 180 to the outer needle hub 18, the pressing projection 186 is configured to be pressed against the inner circumferential surface 28*b* of the outer needle hub 18 (large-diameter tube part 22). Then, the distal end tubular part 182 is elastically deformed to the radially inner side by the pressing reaction force, and the inner circumferential surface 184 of the distal end tubular part 182 is configured to come into contact with the outer circumferential surface 42*c* of the straight part 38*c* of the tubular protrusion 38, so as to provide sealing between the valve member 180 and the outer needle hub 18. That is, in this mode, the sealing face is constituted by the inner circumferential surface 184 of the distal end tubular part 182. In addition, the guide surface that guides the movement of the valve member 180 toward the distal end side can be constituted by the inner circumferential surface 184 of the distal end tubular part 182.

However, the outer circumferential guiding projection, the pressing projection, the compressing projection, the annular sealing projection, and the clamping fit part are not essential in the present invention. That is, for example, in the case where the outer circumferential guiding projection, the pressing projection, and the compressing projection are not provided on the outer circumferential surface of the valve member, the outer circumferential surface of the valve member having a generally straight shape may be in contact with the inner circumferential surface of the needle hub over the entire face, or does not have to be in contact with the inner circumferential surface of the needle hub over the entire face. Besides, in the case where the annular sealing projection and the clamping fit part are not provided on the inner circumferential surface of the distal end tubular part, the inner circumferential surface of the distal end tubular part having a generally straight shape may be in contact with the outer circumferential surface of the protrusion over the entire face, or does not have to be in contact with the outer circumferential surface of the protrusion.

Furthermore, in the preceding practical embodiments, the concave groove 37 is provided on the inner circumferential surface 28*b* of the outer needle hub 18, and the gap 67 between the concave groove 37 and the outer circumferential guiding projection (compressing projection) 62 constitutes the air vent passage. However, in the case where the outer circumferential guiding projection, the pressing projection, and the compressing projection are provided partially in the circumferential direction, the air vent passage may be constituted by the gap formed between the outer circumferential surface of the valve member and the inner circumferential surface of the needle hub at the position away from the outer circumferential guiding projection, the pressing projection, and the compressing projection in the circumferential direction without providing the concave groove 37 on the inner circumferential surface of the needle hub. That is, the air vent passage may be constituted by forming the concave groove 37 on the inner circumferential surface 28*b* of the outer needle hub 18 as in the preceding practical embodiment, or alternatively by forming the concave groove on the outer circumferential surface of the valve member, or for example, by adopting a through hole that penetrates the valve member in the axial direction. Alternatively, it would also be acceptable to adopt a structure which can discharge the air to the outside by providing the needle hub with a through hole by which the space further on the distal end side and on the radially outer side than the distal end tubular part of a valve member communicates with the outside space.

However, such an air vent passage is not essential in the present invention. If the air vent passage is not formed, the space further on the distal end side and on the radially outer side than the distal end tubular part of the valve member is a sealed region. Thus, as described above, when the male connector is inserted and the valve member moves to the distal end side, the effect of the air spring is obtained, and due to the effect of the air spring, the valve member may be configured to return to the original position accompanying the removal of the male connector. That is, the returning means for returning the valve member to the original position may be constituted by the effect of the air spring in the space further on the distal end side and on the radially outer side than the distal end tubular part of the valve member, which is the sealed region.

In the preceding practical embodiments, in the initial state shown in FIGS. 1 to 3, 5A and 5B, 6, 8A to 8C, 9A and 9B (before the male connector 108 is inserted), the protruding tip end face of the tubular protrusion 38 and the distal side end face 50 of the central valve part 46, 124 of the valve member 44, 122, 142, 162 are in contact with each other, but they may be remote from and in opposition to each other with a predetermined axial distance.

Moreover, a sleeve-like separate member that guides the axial movement of the valve member, for example, may be provided radially between the needle hub and the valve member.

Furthermore, as described above, the tubular protrusion 38 in the preceding practical embodiments may have various tubular shapes such as a rectangular tube shape and an elliptical tube shape other than the illustrated circular tube shape. It would be acceptable as long as the tubular protrusion is a member that can open the valve member by its movement. Thus, for example, in the case of separately providing a communication hole for placing the center hole of the outer needle main body 16 in communication with the inside of the outer needle hub 18, it would also be possible to adopt a solid protrusion that is not hollow instead of the tubular protrusion 38.

Additionally, in the preceding practical embodiments, the outer needle (valved needle assembly) 10 is used as the indwelling needle assembly 14 in combination with the inner needle 12. However, in the case where the outer needle main body 16 is formed of a hard member, for example, the valved needle assembly 10 can be used alone.

Besides, a known valve member may be adopted as a valve member that is configured to come into close contact with the protrusion that is integrally formed with the needle hub and extends toward the proximal end side. For example, by adopting a valve member as described in JP-A-2004-242763, the inner circumferential surface of the distal end tubular part of the valve member may be in close contact with the outer circumferential surface of the straight part formed in the axially middle section of the protrusion.

In the present invention, the structure of the needle tip protector that protects the needle tip of the inner needle main body is not limited in any way. For example, the arm piece which protects the needle tip of the inner needle main body may be configured so as not to be located within the outer needle hub. Also, instead of a safety mechanism of a type in which the safety mechanism automatically operates by pulling out the inner needle, it would also be acceptable to adopt a safety mechanism etc. of a type in which, by pressing the button, the inner needle main body moves to the proximal end side of the inner needle hub due to a coil spring or the like, so that the tip of the inner needle main body is housed within the inner needle hub.

Further in the preceding practical embodiments, there is formed the annular gap between the proximal end tubular part 56, 128 as well as the distal end tubular part 52, 126 of the valve member 44, 122, 142, 162, and the inner circumferential surface 28*b* of the outer needle hub 18. The gap also serves to reduce the sliding resistance when the valve member moves in the axial direction within the needle hub, but the shape of the gap does not have to be an annular shape that continues around the entire circumference. For example, by providing a plurality of axial ribs extending in the axial direction on the inner circumferential surface of the needle hub, an axial gap extending between the axial ribs adjacent in the circumferential direction may be provided, or by providing a plurality of axial ribs extending in the axial direction on the outer circumferential surface of the valve member, a similar axial gap may be provided. Alternatively, a valve member may have an outer circumferential surface of generally the same diameter as that of the inner circumferential surface of the needle hub to the extent that a sealing face is not formed therebetween, so that no gap is provided between the needle hub and the proximal end tubular part or the distal end tubular part.

Furthermore, in the preceding practical embodiments, the central valve part 46, 124 is compressed in the radially inward direction almost in its entirety by the outer needle hub 18, but may be only compressed in the direction in which the slit is closed. For example, it would also be possible to provide the compressing projections of the central valve part only on the portions located on the opposite sides in the direction of expansion of the slit (for example, in the first practical embodiment, the opposite sides in the vertical direction in FIG. 1). Further, the compression in the radially inward direction exerted from the needle hub to the central valve part acts at the position before the axial movement of the valve member so as to stabilize the closed state of the slit, while acting at the position after the movement so as to improve the sealing between the central valve part and the inner circumferential surface of the needle hub or the like. Therefore, in the preceding practical embodiment, the compressing projection 62 is compressed by the inner circumferential surface 28*b* of the outer needle hub 18 (large-diameter tube part 22) both before and after the movement of the valve member 44, 122, 142, 162 to the distal end side. However, the compression in the radially inward direction exerted from the needle hub to the central valve part can be performed at least one of before and after the movement of the valve member in the axial direction. That is, for example, the inner circumferential surface of the needle hub may have a tapered surface shape that gradually decreases in inside diameter dimension toward the distal end side. With this configuration, before the movement of the valve member to the distal end side, the compressing projection may be in a non-compressed state, while due to movement of the valve member to the distal end side, the compressing projection may be compressed by the inner circumferential surface of the needle hub.

In order to suitably attach the valve member to the needle hub, it would also be acceptable to provide a mechanism for positioning the valve member at a specific position in the needle hub. Such a mechanism may be realized by, for example, providing a contact projection that projects in an annular shape or partially in the circumferential direction inside the needle hub, and by the contact projection and the projection such as the outer circumferential guiding projection or the compressing projection, for example, which is provided on the outer circumferential surface of the central valve part or the like, coming into contact with each other in the axial direction so as to position the valve member. Further, for example, it would also be acceptable to provide an engagement projection that projects in an annular shape or partially in the circumferential direction inside the needle hub, while providing an engagement groove that extends in the circumferential direction on the outer circumferential surface of the proximal end tubular part or the like of the valve member, so that the engagement projection and the engagement groove come into engaging contact with each other thereby positioning the valve member in the axial direction. Note that the engagement projection and the engagement groove may be replaced by each other. Moreover, for example, it would also be possible to configure such that the inner needle hub and the needle tip protector are inserted into the needle hub so as to be attached or mounted thereto, and the distal ends of the inner needle hub and the needle tip protector serve as positioning tubular parts that come into contact with the valve member from the proximal end side. By inserting the positioning tubular parts into the needle hub, the valve member is configured to be positioned at the predetermined position, whereby the attachment position of the valve member within the needle hub may be determined according to the insertion length or the insertion position of the positioning tubular parts with respect to the needle hub. Furthermore, for example, it would also be possible to configure such that the protruding tip end face of the protrusion that protrudes to the proximal end side in the needle hub has a flat contact face that spreads in an annular shape with a predetermined radial width. By the contact face being contacted by, for example, the distal side end face of the central valve part of the valve member, the axial position of the valve member in the needle hub may be determined. In addition, the tip end face of the protrusion that protrudes to the proximal end in the needle hub does not necessarily have a flat surface, and as long as a certain degree of strength is set to the central valve part by, for example, increasing its thickness or the like, the position of the valve member can be determined by the central valve part of the valve member contacting the tip end of the protrusion. Besides, by changing the thickness of the central valve part, it is also possible to adjust the axial position of the valve member, or to meet the change in axial length of the protrusion without changing the position of the valve member, or the like.

Further, it would also be acceptable to provide a mechanism for preventing the valve member from moving toward the proximal end side within the needle hub due to pressure such as blood pressure after the attachment of the valve member to the needle hub. Such a mechanism may be realized by, for example, providing a positioning projection that projects in an annular shape or partially in the circumferential direction inside the needle hub, and by the positioning projection coming into contact with the projection such as the outer circumferential guiding projection or the compressing projection, for example, which is provided on the outer circumferential surface of the central valve part or the like, so as to limit the movement of the valve member to the proximal end side in the axial direction. Besides, for example, it would also be acceptable to provide a positioning projection that projects in an annular shape or partially in the circumferential direction inside the needle hub, while providing a mating groove that extends in the circumferential direction on the outer circumferential surface of the central valve part or the like of the valve member, so that the positioning projection and the mating groove come into locking contact with each other, thereby limiting the movement of the valve member to the proximal end side in the axial direction. Note that the positioning projection and the mating groove may be replaced by each other. Moreover, for example, it would also be possible to provide a positioning projection that projects in an annular shape or partially in the circumferential direction inside the needle hub, and by the positioning projection coming into contact with a projection or an end face provided on the outer circumferential surface of the end of the proximal end tubular part of the valve member, the movement of the valve member to the proximal end side in the axial direction may be limited. Furthermore, for example, in the case of attaching a member separate from the valve member (a support member, namely, a pusher provided as a separate member on the proximal end side of the proximal end tubular part, for example, or a sleeve-like member for guiding the axial movement of the valve member) in the needle hub, it would also be acceptable to provide the support member with a protrusion or the like for limiting the movement of the valve member to the proximal end side in the axial direction by coming into contact with the projection such as the outer circumferential guiding projection or the compressing projection provided on the central valve part, or the end face of the proximal end tubular part of the valve member, or the like. In that case, for example, a conceivable mode is such that the support member is attached so as to be located on the proximal end side of the central valve part in the needle hub, or the like.

Additionally, in the valve member, the outer circumferential surface of the proximal end tubular part or the like can be shaped along the inner circumferential surface of the needle hub, and for example, may have a tapered surface shape along the inner circumferential surface in the case where the inner circumferential surface of the needle hub is tapered. In addition, in the case of adopting a mechanism in which the valve member returns to the initial position after the male connector is removed, it would also be acceptable to provide a rib projecting on the outer circumferential surface of the proximal end tubular part of the valve member, and when the protrusion protruding to the proximal end side in the needle hub is inserted into the slit of the central valve part, by the rib being compressed, an auxiliary elastic force in the direction of closing the slit may be applied to the central valve part. Moreover, it would also be acceptable to provide a rib projecting on the outer circumferential surface of the proximal end tubular part of the valve member, and when the protrusion protruding to the proximal end side in the needle hub is inserted into the slit of the central valve part, by the rib being further compressed by the inner circumferential surface of the needle hub, a compression force in the direction of tightening the protrusion from the radially outer side may be applied, via the proximal end tubular part, to the central valve part that is bent so as to overlap the inner circumferential surface of the proximal end tubular part.

In the preceding practical embodiment, the central valve part 46, 124 has a disk shape with a generally constant thickness dimension. However, in order to improve pressure resistance against pressure from the distal end side, in the central valve part, only the thickness dimension of the central portion may be increased to the proximal end side. That is, for example, on the proximal end side (proximal side end face) of the central portion of the central valve part, on both sides of the slit, for example, thick portions that are semicircular when viewed in the axial direction may be provided. However, the shape of the thick portion is not limited at all, but various shapes such as a circular shape (including an oval, an ellipse, etc.) and a polygonal shape can be adopted.

Moreover, in the preceding practical embodiment, when the tubular protrusion 38 is inserted into the slit 48 of the central valve parts 46, 124, the central valve part 46, 124 are bent to the proximal end side, so as to be in close contact with the outer circumferential surface 42. In this respect, there may be provided a feature for improving seal strength between the protrusion protruding from the needle hub to the proximal end and the central valve part. That is, for example, it would also be acceptable to provide a thick portion enlarged in thickness dimension on the proximal end side (proximal side end face) of the central portion of the central valve part, and when the protrusion is inserted into the slit of the central valve part, the thick portion may come into contact with the inner circumferential surface of the proximal end tubular part so that the central valve part including the thick portion is compressed between the proximal end tubular part and the protrusion. By so doing, a force can be exerted radially inwardly on the central valve part, thereby improving the seal strength between the protrusion and the central valve part. Alternatively, it would also be acceptable to provide a thick portion enlarged in thickness dimension on the inner circumferential surface of the proximal end tubular part, and when the protrusion is inserted into the slit of the central valve part, the thick part may come into contact with the proximal end side (proximal side end face) of the central portion of the central valve part so that the central valve part is compressed between the proximal end tubular part including the thick portion and the protrusion. By so doing, a force can be exerted radially inwardly on the central valve part, thereby improving the seal strength between the protrusion and the central valve part.

Furthermore, in the preceding first practical embodiment, the axial dimension of the distal end tubular part 52 of the valve member 44 is set such that even when the valve member 44 is moved to the distal end side, the distal end of the distal end tubular part 52 will not hit the inner surface (proximal side end face 28*c*) of the intermediate wall 24 of the outer needle hub 18. However, the present invention is not limited to this mode. That is, as in the preceding second practical embodiment, the distal end of the distal end tubular part may be in contact with the distal end inside the needle hub, namely, for example, the inner surface (proximal side end face) of the intermediate wall in the initial state, or may extend so as to come into contact therewith due to movement of the valve member to the distal end side. In such a case, for example, it would be possible to adopt a structure in which the inner circumferential surface of the distal end of the distal end tubular part (for example, annular sealing projection) comes into contact with only the outer circumferential surface of the axially distal end section of the protrusion protruding from the needle hub to the proximal end side (protruding base end) in a compressed state about the entire circumference, and these contact surfaces each comprise an annular sealing face. The sealing face can be realized by, for example, dimensional design, that is, in the isolated state of the valve member before being attached to the needle hub, the inside diameter dimension of the inner circumferential surface of the distal end of the distal end tubular part (for example, the annular sealing projection) is set smaller than the outside diameter dimension of the outer circumferential surface at the axially distal end section of the protrusion (protruding base end). In the case where such a valve member is adopted, by an external instrument such as a male connector being inserted from the proximal end side of the needle hub so that the proximal end tubular part is pressed to the distal end side, the central valve part and the proximal end tubular part can be moved to the distal end side accompanied by deformation in the radial direction of the lengthwise middle portion of the distal end tubular part. By so doing, the protrusion can be inserted into the slit of the central valve part, so as to push the slit open. In such a specification, from the perspective of improvement in position stability of the valve member, it is preferable that the portion other than the distal end of the distal end tubular part of the valve member has such an internal shape as to come into contact with the protrusion to the extent that a sealing face will not be formed.

Indeed, in the present invention, the distal end tubular part of the valve member is not essential. That is, the valve member may be arranged in the needle hub without fitting on the outer circumferential surface of the protrusion protruding to the proximal end side. For example, the entirety of the valve member including the proximal end tubular part may be positioned further on the proximal end side than the protruding tip portion of the protrusion. In such a case, the distal side end face of the valve member is a flat surface that extends in the axis-perpendicular direction over the entire face, and the distal side end face of the valve member may be located further on the proximal end side than the protruding tip face of the protrusion, or alternatively, the outer circumferential portion of the distal side end face of the valve member may slightly project to the distal end side so that the projecting portion is positioned on the radially outer side of the tip portion of the protrusion. In such a valve member, a mechanism for positioning the valve member at a specific position in the needle hub as described above, or a mechanism for preventing the valve member from moving to the proximal end side within the needle hub can be suitably employed.

In the preceding practical embodiments, the protruding tip end face of the tubular protrusion 38 contacts the distal side end face 50 of the central valve part 46, 124 of the valve member 44, 122, 142, 162, or the outer circumferential guiding projection (compressing projection) 62 provided on the outer circumferential surface 58 of the valve member 44, 122, 142, 162, contacts the inner circumferential surface 28*b* of the outer needle hub 18 (large-diameter tube part 22) in a compressed state, so that the distal end of the valve member 44, 122, 142, 162 is positioned and fixed in the axial direction with respect to the outer needle hub 18. However, the following modes may be employed in addition to or in place of these modes. That is, for example, a projection or the like may be provided on the inner circumferential surface of the needle hub so as to come into contact with the distal end face of the valve member, or to engage with a concave part or a convex part provided on the outer circumferential surface of the valve member, thereby positioning and fixing the distal end of the valve member in the axial direction with respect to the needle hub. Besides, for example, a projection or the like that projects to the radially outer side may be provided on the outer circumferential surface of the distal end tubular part of the valve member, so as to engage with a concave part or a convex part provided on the inner circumferential surface of the needle hub, or to contact the inner circumferential surface of the needle hub in a compressed state, thereby positioning and fixing the distal end of the valve member in the axial direction with respect to the needle hub by the frictional force. Furthermore, for example, it would also be acceptable to attach a member (support member) separate from the valve member to the needle hub, so that the distal end of the valve member may be positioned and fixed in the axial direction with respect to the needle hub. As the support member, for example, a pusher provided on the proximal end side of the valve member, a sleeve-like member for guiding the axial movement of the valve member, or the like can be adopted.

The present invention has a structure in which the entire valve member or a part of the valve member (central valve part and proximal end tubular part) moves in the distal direction by inserting a male connector or the like into the needle hub. In this respect, as described above, it would also be possible to adopt a structure in which, after the male connector or the like is removed from the needle hub, the entire valve member or a part of the valve member (central valve part and proximal end tubular part) moves in the proximal direction. That is, the structure in which the male connector can be connected a plurality of times may be adopted. Conversely, it would also be possible to adopt a structure in which, after the male connector or the like is removed from the needle hub, the entire valve member or a part of the valve member (central valve part and proximal end tubular part) does not move in the proximal direction. That is, the structure in which the male connector can be connected only once may be adopted. The structure in which, after the male connector or the like is removed from the needle hub, the entire valve member or a part of the valve member (central valve part and proximal end tubular part) does not move in the proximal direction may be realized by, for example, forming the valve member with a material having small elastic modulus and minimizing the recovery elastic deformation, or physically engaging projections or the like provided between the outer circumferential surface of the valve member and the inner circumferential surface of the needle hub. Alternatively, a part of the outer circumferential surface of the protrusion protruding from the needle hub to the proximal end side may be provided with a tapered portion that gradually increases in diameter toward the axially proximal end side, so as to make it difficult for the valve member, which has moved to the distal end, to move in the proximal direction.

In the preceding practical embodiment, the air vent passage is constituted by the radially inner side opening of the concave groove 37 provided in the inner circumferential surface 28b of the outer needle hub 18 (large-diameter tube part 22) being covered with the outer circumferential surface 58 of the valve member 44. However, the air vent passage is not limited to the one formed between the inner circumferential surface 28 of the outer needle hub 18 and the outer circumferential surface 58 of the valve member 44. That is, the air in the needle hub may be released from between the needle hub and the outer needle main body (hollow needle) through a through hole penetrating the needle hub, or as described above, a micro hole may be provided so as to penetrate the needle hub inward and outward. Note that in the micro hole, an air-permeable (liquid-impermeable) filter may be provided or an antibacterial agent or the like may be added so that a liquid such as blood will not leak to the outside.

Moreover, in the preceding practical embodiment, the distal end tubular part 52, 126 and the proximal end tubular part 56, 128 all extend straight in the axial direction, but the present invention is not limited to these modes. That is, the distal end tubular part and/or the proximal end tubular part may have a shape that is partially or entirely curved or bent, or may extend generally linearly so as to incline with respect to the axial direction. In the preceding second practical embodiment (the practical embodiment shown in FIGS. 5A to 7), the central valve part 124 and the distal end tubular part 126 are connected by the tapered part 130. However, the portion extending to the distal end side from the central valve part can also be regarded as the distal end tubular part, namely, it would also be possible to grasp that the distal end tubular part is constituted including the tapered part.

Furthermore, in the preceding second practical embodiment, in the mode shown in FIGS. 5A to 7, the mode shown in FIGS. 8A to 8C, and the mode shown in FIGS. 9A and 9B, the sealing faces (the inner circumferential surfaces 134, 146 of the annular sealing projections 132, 144, and the distal end face 129) are respectively formed on the proximal end portion, the distal end portion, and the distal end face of the inner circumferential surface 60a of the distal end tubular part 126, but at least two of them may be adopted in combination.

Additionally, in the all modes of the preceding second practical embodiment, in the initial state before the male connector 108 is inserted, the distal end face 129 of the distal end tubular part 126 and the proximal side end face 28c of the intermediate wall 24 are in contact with each other in the axial direction, and the distal end tubular part 126 is configured to be compressed in the axial direction due to the valve member 122, 142, 162 moving to the distal end side. However, the present invention is not limited to this mode. That is, in the initial state, the distal end face of the distal end tubular part and the proximal side end face of the intermediate wall may be remote from each other, and due to the valve member moving to the distal end side, the distal end face of the distal end tubular part and the proximal side end face of the intermediate wall may come into contact with each other so that the distal end tubular part is compressed in the axial direction.

Further, in the preceding second practical embodiment, in the mode shown in FIGS. 5A to 7 and the mode shown in FIGS. 8A to 8C, the annular sealing projections 132, 144 each projecting radially inward from the inner circumferential surface 60a of the distal end tubular part 126 are provided, and their respective inner circumferential surfaces 134, 146 are in close contact with the outer circumferential surface 42 (42d) of the tubular protrusion 38 (38d) so as to constitute the sealing face. However, the annular sealing projection that provides sealing between the valve member and the protrusion protruding from the needle hub to the proximal end side may project radially outward from the outer circumferential surface of the protrusion so as to be in close contact with the inner circumferential surface of the distal end tubular part.

KEYS TO SYMBOLS 10, 120, 140, 160: outer needle (valved needle assembly), 16: outer needle main body (hollow needle), 18: outer needle hub (needle hub), 28: inner circumferential surface of outer needle hub, 28b: inner circumferential surface of large-diameter tube part, 30: proximal end opening part, 37: concave groove (air vent passage), 38: tubular protrusion (protrusion), 38a: axially proximal end section of protrusion, 38b: axially distal end section of protrusion, 38c: straight part (axially middle section of protrusion), 38d: straight part, 42: outer circumferential surface of protrusion (sealing face), 42a: outer circumferential surface of axially proximal end section of protrusion (tapered sloping face), 42c, 42d: outer circumferential surface of straight part, 42e: distal end outer circumferential surface of protrusion, 44, 122, 142, 162, 170, 180: valve member, 46, 124: central valve part, 48: slit, 52, 126, 182: distal end tubular part, 56, 128: proximal end tubular part, 58: outer circumferential surface of valve member, 60a: inner circumferential surface of distal end tubular part, 60d: distal end of inner circumferential surface of distal end tubular part (sealing face), 62: outer circumferential guiding projection (compressing projection), 64, 132, 144: annular sealing projection (clamping fit part), 66: inner circumferential surface of annular sealing projection (sealing face, guide surface), 67: gap (air vent passage), 68: space, 108: male connector, 129: distal end face (sealing face), 130: tapered part, 134: inner circumferential surface of annular sealing projection (sealing face, guide surface), 136: gap, 146: inner circumferential surface of annular sealing projection (sealing face), 148: overlapping part (connecting part), 150: sloping inner face, 164: flanged part, 172: distal end tubular part (clamping fit part), 174, 184: inner circumferential surface of distal end tubular part (sealing face, guide surface), 186: pressing projection

The invention claimed is:
1. A valved needle assembly comprising:
a hollow needle;
a needle hub provided to a proximal end side of the hollow needle; and
a valve member incorporated inside the needle hub and blocking communication with the hollow needle, wherein
a protrusion is provided inside the needle hub and protrudes from a distal end side toward a proximal end side, and the valve member blocks the proximal end side of the protrusion inside the needle hub, a central valve part of the valve member positioned in opposition to the protrusion and having a slit is configured to be moved toward the protrusion such that the slit is opened and placed in a communicating state by the protrusion, the central valve part is provided with a distal end tubular part extending from an outer circumferential portion thereof toward the distal end side, and a proximal end tubular part extending from the outer circumferential portion thereof toward the proximal end side, and the valve member includes an outer circumferential guiding projection projecting radially outward from an outer circumferential surface of the central valve part and configured to move in contact with an inner circumferential surface of the needle hub.

2. The valved needle assembly according to claim 1, wherein an inner circumferential surface of the distal end tubular part of the valve member includes a guide surface that is in contact with an outer circumferential surface of the protrusion of the needle hub.

3. The valved needle assembly according to claim 1, wherein the protrusion of the needle hub comprises a tubular protrusion formed in a tubular shape, and an inner circumferential surface of the distal end tubular part of the valve member includes a sealing face that is in contact with an outer circumferential surface of the tubular protrusion of the needle hub about an entire circumference.

4. The valved needle assembly according to claim 3, wherein the distal end tubular part of the valve member includes an annular sealing projection projecting toward a radial inside, and an inner circumferential surface of the annular sealing projection comprises the sealing face.

5. The valved needle assembly according to claim 3, wherein the distal end tubular part of the valve member includes a clamping fit part fitted externally onto the tubular protrusion in an expanded state in which the clamping fit part is pushed open, and an inner circumferential surface of the clamping fit part comprises the sealing face.

6. The valved needle assembly according to claim 3, wherein the distal end tubular part of the valve member includes a pressing projection projecting on an outer circumferential surface of the distal end tubular part and pressed against the inner circumferential surface of the needle hub, and the inner circumferential surface of the distal end tubular part is brought into contact with the outer circumferential surface of the tubular protrusion by a pressing reaction force of the pressing projection against the needle hub such that the sealing face is constituted.

7. The valved needle assembly according to claim 3, wherein in the distal end tubular part of the valve member, a portion that does not constitute the sealing face is longer than a portion that constitutes the sealing face, and due to the central valve part of the valve member being moved toward the protrusion of the needle hub, the portion that does not constitute the sealing face is configured to deform in a corrugated shape in a lengthwise direction such that a length of the distal end tubular part is shortened.

8. The valved needle assembly according to claim 1, wherein an outer circumferential surface of the valve member includes a compressing projection exerting a compression force on the slit of the valve member in a direction of closing by utilizing a contact reaction force against the needle hub due to contact with the inner circumferential surface of the needle hub.

9. The valved needle assembly according to claim 1, wherein an air vent passage is provided and configured to discharge air in a space located in front of the valve member within the needle hub to an outside when the valve member moves to the distal end side within the needle hub.

10. The valved needle assembly according to claim 1, wherein in the valve member, the distal end tubular part is thinner than the proximal end tubular part.

11. The valved needle assembly according to claim 1, wherein the distal end tubular part of the valve member has a length that covers the protrusion of the needle hub as far as a distal end thereof.

12. The valved needle assembly according to claim 1, wherein the valve member includes a tapered part that gradually decreases in diameter from the central valve part toward the distal end tubular part, and on a radially inner side of the tapered part, a gap is provided between the tapered part and the protrusion of the needle hub.

13. The valved needle assembly according to claim 1, wherein an outer circumferential surface of a protruding end of the protrusion of the needle hub includes a tapered sloping face that gradually decreases in diameter toward the central valve part, and the valve member includes an overlapping part having a sloping inner face that gradually decreases in diameter from the distal end tubular part toward the central valve part while being in contact and overlapped with the tapered sloping face of the protrusion.

14. The valved needle assembly according to claim 1, wherein the valve member includes a connecting part that gradually increases in thickness dimension from the distal end tubular part toward the central valve part.

15. A valved needle assembly comprising:

a hollow needle;

a needle hub provided to a proximal end side of the hollow needle; and a valve member incorporated inside the needle hub and blocking communication with the hollow needle, wherein a protrusion is provided inside the needle hub and protrudes from a distal end side toward a proximal end side, and the valve member blocks an inside of the needle hub, a central valve part of the valve member positioned in opposition to the protrusion and having a slit is configured to be moved toward the protrusion such that the slit is opened and placed in a communicating state by the protrusion, the central valve part is provided with a proximal end tubular part extending from an outer circumferential portion thereof toward the proximal end side, and a compression force is exerted on an outer circumferential surface of the central valve part due to contact against the needle hub, and the valve member includes an outer circumferential guiding projection projecting radially outward from the outer circumferential surface of the central valve part and configured to move in contact with an inner circumferential surface of the needle hub.

16. The valved needle assembly according to claim 15, wherein an entirety of the valve member including the central valve part provided with the proximal end tubular part is positioned further on the proximal end side than a tip portion of the protrusion and housed inside the needle hub without fitting on an outer circumferential surface of the protrusion.

17. A valved needle assembly comprising:
a hollow needle;
a needle hub provided to a proximal end side of the hollow needle; and
a valve member incorporated inside the needle hub and blocking communication with the hollow needle, wherein
a protrusion is provided inside the needle hub and protrudes from a distal end side toward a proximal end side, and the valve member blocks an inside of the needle hub,
a central valve part of the valve member positioned in opposition to the protrusion and having a slit is configured to be moved toward the protrusion such that the slit is opened and placed in a communicating state by the protrusion,
the central valve part is provided with a distal end tubular part extending from an outer circumferential portion thereof toward the distal end side, and a proximal end tubular part extending from the outer circumferential portion thereof toward the proximal end side,
the distal end tubular part extends as far as a distal end of the inside of the needle hub, and the distal end tubular part includes a sealing face that is in contact with a distal end outer circumferential surface of the protrusion about an entire circumference, and
the valve member includes an outer circumferential guiding projection projecting radially outward from an outer circumferential surface of the central valve part and configured to move in contact with an inner circumferential surface of the needle hub.

18. The valved needle assembly according to claim 17, wherein
the distal end tubular part is in contact with only the distal end outer circumferential surface of the protrusion about the entire circumference in a compressed state, and
due to the proximal end tubular part being pressed to the distal end side by an external instrument, a lengthwise middle portion of the distal end tubular part is configured to deform in a radial direction.

19. The valved needle assembly according to claim 1, wherein the outer circumferential guiding projection has an outside diameter dimension larger than those of the distal end tubular part and the proximal end tubular part.

20. The valved needle assembly according to claim 15, wherein the outer circumferential guiding projection has an outside diameter dimension larger than that of the proximal end tubular part.

* * * * *